United States Patent
Hisada et al.

(10) Patent No.: US 7,153,701 B1
(45) Date of Patent: Dec. 26, 2006

(54) METHOD FOR QUANTITATIVELY DETECTING ANTIGEN

(75) Inventors: Sunao Hisada, Shizuoka (JP); Yukiko Ito, Shizuoka (JP); Hiroyuki Matsumoto, Shizuoka (JP); Kiyohito Shimura, Kanagawa (JP); Kenichi Kasai, Kanagawa (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 0 days.

(21) Appl. No.: 09/622,206

(22) PCT Filed: Feb. 17, 2000

(86) PCT No.: PCT/JP00/00903

§ 371 (c)(1),
(2), (4) Date: Jun. 21, 2001

(87) PCT Pub. No.: WO01/61351

PCT Pub. Date: Aug. 23, 2001

(51) Int. Cl.
*G01N 33/561* (2006.01)
*G01N 33/537* (2006.01)
*G01N 33/563* (2006.01)
*C07K 16/00* (2006.01)
*C12P 21/08* (2006.01)

(52) U.S. Cl. ............... 436/516; 435/7.1; 435/69.1; 435/70.21; 435/328; 436/512; 436/517; 436/538; 436/548; 436/166; 436/172; 530/387.3; 530/391.1; 530/391.3; 530/391.5; 536/23.53

(58) Field of Classification Search .......... 435/7.1, 435/69.1, 70.21, 328, 964; 436/512, 516, 436/517, 538, 547, 548, 166, 172; 530/387.3, 530/391.1, 391.3, 391.5, 866; 536/23.53
See application file for complete search history.

(56) References Cited

U.S. PATENT DOCUMENTS

| | | | | |
|---|---|---|---|---|
| 4,816,567 A | * | 3/1989 | Cabilly et al. | 530/387.3 |
| 5,019,521 A | | 5/1991 | Krupey | |
| 5,348,633 A | * | 9/1994 | Karger et al. | 204/452 |
| 5,630,924 A | * | 5/1997 | Fuchs et al. | 204/601 |

FOREIGN PATENT DOCUMENTS

| | | | |
|---|---|---|---|
| JP | 5-322892 | | 12/1993 |
| JP | 11-127855 | | 5/1999 |
| WO | 89/01974 | * | 3/1989 |

OTHER PUBLICATIONS

Chen et al., 1994. Characterization of proteins by capillary electrophoresis in fused-silica columns: review on serum protein analysis and application to immunoassays. Electrophoresis 15: 13-21.*
Shimura et al., 1994. Affinity probe capillary electrophoresis: analysis of recombinant human growth hormone with a fluorescent labeled antibody fragment. Anal. Chem. 66: 9-15.*
Kiyohito Shimura, "Affinity Probe Capillary Electrophoresis: Antigen Quantification and Analysis of Specific Interaction.", Japanese Journal of Electrophoresis, 1995, vol. 39, No. 6, pp. 349-353. Abstract only.

* cited by examiner

*Primary Examiner*—Christopher L. Chin
*Assistant Examiner*—James L. Grun
(74) *Attorney, Agent, or Firm*—Leydig, Voit & Mayer

(57) ABSTRACT

A method for quantitatively detecting an antigen which comprises (1) a first step of providing an Fab' antibody having a uniform isoelectric point, said antibody forming an immune complex with an antigen in an analytical sample and being modified by adding an amino acid sequence comprising a charged amino acid residue and by being labeled with a fluorescent dye, (2) a second step of mixing the Fab' antibody having a uniform isoelectric point with the analytical sample containing the antigen to obtain a mixture comprising the immune complex, (3) a third step of separating the mixture by performing electrophoresis in a carrier, (4) a fourth step of irradiating an excitation light which excites the fluorescent dye to the mixture separated in the third step to cause fluorescence in the immune complex, and (5) a fifth step of detecting the fluorescence.

4 Claims, 8 Drawing Sheets

図7A
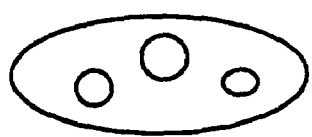 
図7B
図7C
 
図7D
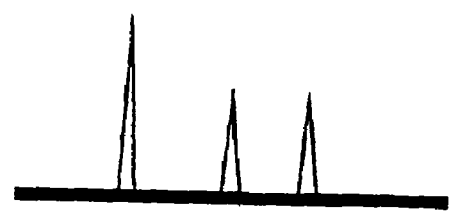

図8A 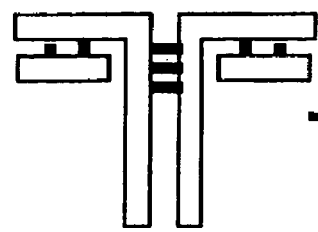 図8B 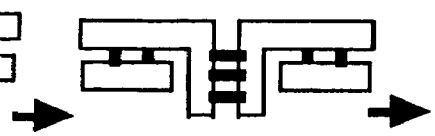 図8C 
図8D 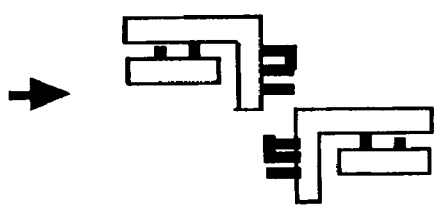 図8E 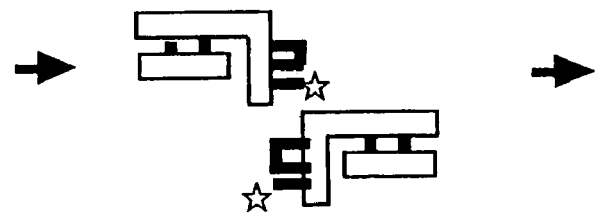
図8F 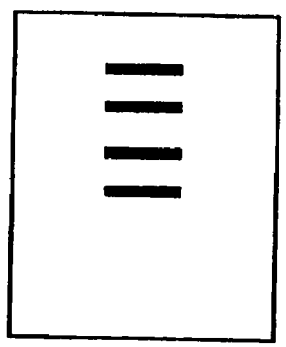 図8G 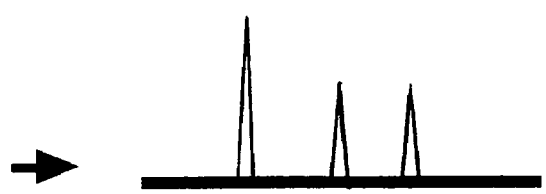

METHOD FOR QUANTITATIVELY DETECTING ANTIGEN

TECHNICAL FIELD

This invention relates to a method for quantitatively detecting an antigen, more specifically, to a method for quantitatively detecting an antigen using an Fab' antibody having a uniform isoelectric point, said antibody forming an immune complex with an antigen in an analytical sample and being modified by adding an amino acid sequence comprising a charged amino acid residue and by being labeled with a fluorescent dye.

BACKGROUND ART

When electric field is supplied to a charged substance in an electrolyte solution, the substance migrates toward the electrode having an opposite charge of the substance. This phenomenon, electrophoresis, is widely used as a means for separating various substances. Generally, electrophoresis of an analytical sample is performed in a carrier having a constant pH. On the contrary, a carrier having a gradient pH is used when electrophoresis is performed based on the isoelectric focusing method. Since the isoelectric focusing method was developed, it has been acquiring popularity as a means for separating amphoteric electrolytes, such as amino acids and proteins.

An amphoteric electrolyte has a pH value where its effective charge becomes zero, and the pH value is called an isoelectric point. When electrophoresis of the analytical sample consisting of an amphoteric electrolyte is performed based on the isoelectric focusing method, the sample stops at a certain position in an electrophoresis carrier and is concentrated there. This position is where a pH value of the electrophoresis carrier is equal to the isoelectric point of the sample. In this case, the separated sample is concentrated in a focusing manner, therefore, the isoelectric focusing method has very high separability.

Recently, the capillary electrophoresis, where electrophoresis is performed in a capillary having an inside diameter of several 10 micrometers and a length of several 100 milimeters, was established. Using this method, very high separability is obtained with a very small amount of analytical sample. Therefore, the method is applied to separation and analysis of various samples including proteins, inorganic ions, low molecular compounds, nucleic acids, and the like. When the capillary electrophoresis is performed, concentration of the separated analytical sample can be quantified using a detector equipped at one end of the capillary.

Detection of the sample separated by the electrophoresis is generally done by the ultraviolet/visible detecting method that includes irradiation of an ultraviolet light or a visible light to the sample and measurement of the changes of the amount of light absorbed. Detection can be done with higher sensitivity when a fluorescence detection method is applied. In the fluorescence detection method, an analytical sample is labeled with a fluorescent dye (fluorescently labeling). In this method, an excitation light is focused on the separated sample, and fluorescence generated is detected to quantify the concentration of the sample.

It is possible to combine above-mentioned isoelectric focusing method, capillary electrophoresis, and fluorescence detection method. The combined method is called fluorescently detecting capillary isoelectric focusing. In the case of fluorescently detecting capillary isoelectric focusing, electrophoresis is performed to the fluorescently labeled sample in a carrier having a gradient pH, which is held in the capillary, and the fluorescence caused by irradiation of an excitation light is detected with an optical detector or the like. According to this method, even with the sample of a very small amount, a highly precise quantitative detection is possible. Therefore, this method attracts attention as a super-high-sensitive analytical method for proteins or the like.

In recent years, in many cases, a minor constituent in a living body is analyzed by the electrophoresis mentioned above. When performing such analysis, an immune complex formed by reacting a minor constituent in a living body with the antibody that recognizes the minor constituent as an antigen is detected. The immune complex is preferably labeled with a fluorescent dye for the purpose of accurate detection. In this case, either the antigen or the antibody needs to be fluorescently labeled. Upon labeling the antigen or the antibody using the fluorescent dye, conventional labeling method can not be applied for the following reasons.

Antibodies and many antigens are composed of proteins. The number of amino groups at an N-terminal of a protein and at a lysine side chain, and the dissociated state thereof are great factors in determining the isoelectric point of a protein (Zokuseikagaku Jikkenkoza 2, Chemistry of proteins, volume 1, Society of Japan Biochemistry, 1987). Therefore, the conventional labeling method utilizing a reaction between a fluorescent dye and an amino group of a protein greatly changes the isoelectric point of a protein.

In addition, the number and position of a fluorescent dye bound to a protein become indefinite because there are a large number of amino acids that are reactive with a fluorescent dye in a protein. Accordingly, the resultant protein becomes a mixture of proteins showing different isoelectric point, which makes it difficult to conduct a precise analysis using the isoelectric focusing. Further, since the three-dimensional structure of a protein is changed by a fluorescent dye, there is also a problem that the chemical stability of a protein itself is deteriorated.

In addition, there is a situation where an analysis by isoelectric focusing can not be done with high accuracy even when a monoclonal antibody having a uniform molecular weight obtained by a hybridoma is used as an antibody for detection. This is because the monoclonal antibody having a uniform molecular weight produced by hybridoma does not necessarily have a uniform isoelectric point, and this phenomenon is called microheterogeneity (Bouman H et al., Z Immunitatsforsch Exp Klin Immunol. 1975 October; 150 (4): 370–7).

As reasons for this non-uniformity of isoelectric point, deamidation of a protein (Robinson A. B. et al., Proc. Natl. Acad. Sci. U.S.A. 1970 July; 66 (3): 753–7), pyroglutamylation of an N-terminal (Scott D. I. Et al., Biochem J. 1972 August; 128(5): 1221–7), addition of a sugar chain (Cohenford M. A. et al. Immunol. Commun. 1983; 12(2): 189–200), myristoylation (Pillai S. et al., Proc. Natl. Acad. Sci. U.S.A. 1987 November; 84(21): 7654–8) and the like have been proposed, but the mechanism for the non-uniformity of the isoelectric point of a protein has not been specified yet.

Therefore, when an analytical sample shows plural isoelectric points by isoelectric focusing, it is difficult to determine where the plurality originates from. This is because the plurality is ascribable either to an antigen or to an antibody. Both antigen and antibody may have non-uniformity of isoelectric point, as mentioned above.

Therefore, when analysis is performed by electrophoresis utilizing an antigen-antibody reaction, an antibody is necessary to be uniform in terms of isoelectric point, and when an antibody having a uniform isoelectric point is fluorescently labeled with a fluorescent dye, the fluorescent dye should not be reacted with an amino group of the antibody as described above.

Shimura K. and Karger B. L. disclose a method for quantitatively detecting an antigen using an antibody having a uniform isoelectric point, (see Anal. Chem. 1994 Jan. 1; 66(1): 9–15, or JP-A 8-506182). The method disclosed in these references is schematically shown in FIGS. 8A to G. That is, IgG antibody produced by a hybridoma (FIG. 8A) is cut with a protease (pepsin) and the resulting F (ab')$_2$ antibody (FIG. 8B) is separated. This is treated with a reducing agent of mercaptoethylamine to reduce three disulfide bonds (S—S bond) to obtain Fab' antibody (FIG. 8C). This Fab' antibody is oxidized to leave behind only one reactive thiol group (SH group) (FIG. 8D) and a fluorescent dye is bound to this thiol group (FIG. 8E). The resulting fluourescently labeled Fab' antibody is separated by isoelectric focusing and a fluorescently labeled Fab' antibody having a uniform isoelectric point is taken from an electrophoresis carrier (FIG. 8F). The obtained fluorescently labeled Fab' antibody having a uniform isoelectric point is combined with an antigen. Then, electrophoresis is performed, and fluorescence caused by excitation light is measured. (FIG. 8G).

DISCLOSURE OF THE INVENTION

However, the method disclosed by Shimura K and Karger B L, as above, involve steps for obtaining Fab' antibody having a uniform isoelectric point that are complicated. In addition, when an isoelectric point of the antigen, which is the analyte, is close to an isoelectric point of the fluorescently labeled antibody, migration time of the immune complex comprising antigen and antibody becomes almost the same as that of excessive antigen and/or antibody. Therefore, the electrophoretic peaks overlap and detection can not be performed with high accuracy.

The present invention was done in view of the aforementioned problems of the prior art and an object of the present invention is to provide a method for quantitatively detecting an antigen which enables the analysis of the antigen with high accuracy, even when the isoelectric point of the antigen as the analyte is close to that of the fluorescently labeled antibody.

The present inventors studied extensively and, as a result, found that it is possible to analyze an antigen with high accuracy by using an Fab' antibody having a uniform isoelectric point, which has been modified by adding an amino acid sequence comprising a charged amino acid residue and by being labeled with a fluorescent dye, and which forms an immune complex with an antigen in an analytical sample.

That is, the present invention provides a method for quantitatively detecting an antigen which comprises (1) a first step of providing an Fab' antibody having a uniform isoelectric point, said antibody forming an immune complex with an antigen in an analytical sample and being modified by adding an amino acid sequence comprising a charged amino acid residue and by being labeled with a fluorescent dye, (2) a second step of mixing the Fab' antibody having a uniform isoelectric point with the analytical sample containing the antigen to obtain a mixture comprising the immune complex, (3) a third step of separating the mixture by performing electrophoresis in a carrier, (4) a fourth step of irradiating an excitation light which excites the fluorescent dye to the mixture separated in the third step to cause fluorescence in the immune complex, and (5) a fifth step of detecting the fluorescence.

In a method for quantitatively detecting an antigen of the present invention, it is preferred that the amino acid sequence is added adjacent to a C-terminal of an L chain of the Fab' antibody having a uniform isoelectric point. And it is preferred that the fluorescent dye is bound to a cysteine residue which is not involved in binding with an L chain and which exists in an amino acid sequence adjacent to a C-terminal of a CH1 region of the Fab' antibody having a uniform isoelectric point.

In addition, in a method for quantitatively detecting an antigen of the present invention, it is preferred that the electrophoresis is performed by isoelectric focusing and that the electrophoresis is performed by capillary electrophoresis.

Further, it is preferred that the Fab' antibody having a uniform isoelectric point is produced by a method which comprises (1) a first step of providing an Fd chain gene encoding a VH region, a CH1 region, and an amino acid sequence which adjoins to a C-terminal of the CH1 region and comprises a cysteine residue which is not involved in binding with an L chain in an Fab' antibody, (2) a second step of site-specifically mutating in the Fd chain gene at least one codon encoding an amide group-containing amino acid residue in the CH1 region, into a codon encoding an amide group-non-containing amino acid residue except for cysteine to obtain a modified Fd chain gene, (3) a third step of linking the modified Fd chain gene and an L chain gene encoding an L chain of the Fab' antibody in the expressible state to obtain a gene expressing a modified Fab' antibody, (4) a fourth step of modifying the gene expressing a modified Fab' antibody to express an amino acid sequence comprising a charged amino acid residue adjacent to a C-terminal of the L chain to obtain a gene expressing, a charge modified Fab' antibody, (5) a fifth step of transforming a host cell with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region, and (6) a sixth step of binding a fluorescent dye to the cysteine residue which is not involved in binding with an L chain in the Fab' antibody having a uniform isoelectric point obtained in the fifth step.

In addition, it is preferred that the Fab' antibody having a uniform isoelectric point is produced by a method which comprises (1) a first step of providing an Fd chain gene encoding a VH region, a CH1 region, and an amino acid sequence which adjoins to a C-terminal of the CH1 region and comprises a cysteine residue which is not involved in binding with an L chain in an Fab' antibody, (2) a second step of site-specifically mutating in the Fd chain gene at least one codon encoding an amide group-containing amino acid residue in the CH1 region, into a codon encoding an amide group-non-containing amino acid residue except for cysteine to obtain a modified Fd chain gene, (3) a third step of providing an L chain gene encoding an L chain of the Fab' antibody, (4) a fourth step of modifying the L chain gene to express an amino acid sequence comprising a charged amino acid residue adjacent to a C-terminal of the L chain to obtain a charge modified L chain gene, (5) a fifth step of linking the modified Fd chain gene and the charge modified L chain gene in the expressible state to obtain a gene expressing a charge modified Fab' antibody, (6) a sixth step of transforming a host cell with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region, and (7) a seventh step of binding a fluorescent dye to the cysteine residue which is not involved in binding with an L chain in the Fab' antibody having a uniform isoelectric point obtained in the sixth step.

Further, it is preferred that the Fab' antibody having a uniform isoelectric point is produced by a method which comprises (1) a first step of providing an Fd chain gene encoding a VH region, a CH1 region, and an amino acid sequence which adjoins to a C-terminal of the CH1 region and comprises a cysteine residue which is not involved in binding with an L chain in an Fab' antibody, and an L chain gene encoding the L chain of the Fab' antibody, (2) a second step of linking the Fd chain gene and the L chain gene in the expressible state to obtain a gene expressing an Fab' antibody, (3) a third step of modifying the gene expressing an Fab' antibody to express an amino acid sequence comprising a charged amino acid residue adjacent to a C-terminal of the L chain, and site-specifically mutating in the gene expressing an Fab' antibody at least one codon encoding an amide group-containing amino acid residue in the CH1 region, into a codon encoding an amide group-non-containing amino acid residue except for cysteine to obtain a gene expressing a charge modified Fab' antibody, (4) a fourth step of transforming a host cell with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region, and (5) a fifth step of binding a fluorescent dye to the cysteine residue which is not involved in binding with an L chain in the Fab' antibody having a uniform isoelectric point obtained in the fourth step.

Furthermore, it is preferred that the Fab' antibody having a uniform isoelectric point is produced by a method which comprises (1) a first step of providing a CH1 gene encoding a CH1 region and an amino acid sequence which adjoins to a C-terminal of the CH1 region and comprises a cysteine residue which is not involved in binding with an L chain in a first Fab' antibody, and a CL gene encoding a CL region of the first Fab' antibody, (2) a second step of site-specifically mutating in the CH1 gene at least one codon encoding an amide group-containing amino acid residue in the CH1 region, into a codon encoding an amide group-non-containing amino acid residue except for cysteine to obtain a modified CH1 gene, (3) a third step of cutting the modified CH1 gene with a restriction enzyme to obtain a gene fragment encoding the CH1 region, (4) a fourth step of providing a VH gene encoding a VH region of a second Fab' antibody and a VL gene encoding a VL region of the second Fab' antibody, (5) a fifth step of linking the gene fragment, the CL gene, the VH gene and the VL gene in the expressible state to obtain a gene expressing a modified Fab' antibody, (6) a sixth step of modifying the gene expressing a modified Fab' antibody to express an amino acid sequence comprising a charged amino acid residue adjacent to a C-terminal of the CL region to obtain a gene expressing a charge modified Fab' antibody, (7) a seventh step of transforming a host cell with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region, and (8) a eighth step of binding a fluorescent dye to the cysteine residue which is not involved in binding with an L chain in the Fab' antibody having a uniform isoelectric point obtained in the seventh step.

In addition, it is preferred that the Fab' antibody having a uniform isoelectric point is produced by a method which comprises (1) a first step of providing a CH1 gene encoding a CH1 region and an amino acid sequence which adjoins to a C-terminal of the CH1 region and comprises a cysteine residue which is not involved in binding with an L chain in a first Fab' antibody, and a CL gene encoding a CL region of the first Fab' antibody, (2) a second step of site-specifically mutating in the CH1 gene at least one codon encoding an amide group-containing amino acid residue in the CH1 region, into a codon encoding an amide group-non-containing amino acid residue except for cysteine to obtain a modified CH1 gene, (3) a third step of cutting the modified CH1 gene with a restriction enzyme to obtain a gene fragment encoding the CH1 region, (4) a fourth step of modifying the CL gene to express an amino acid sequence comprising a charged amino acid residue adjacent to a C-terminal of the CL region to obtain a charge modified CL gene, (5) a fifth step of providing a VH gene encoding a VH region of a second Fab' antibody and a VL gene encoding a VL region of the second Fab' antibody, (6) a sixth step of linking the gene fragment, the charge modified CL gene, the VH gene and the VL gene in the expressible state to obtain a gene expressing a charge modified Fab' antibody, (7) a seventh step of transforming a host cell with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region, and (8) a eighth step of binding a fluorescent dye to the cysteine residue which is not involved in binding with an L chain in the Fab' antibody having a uniform isoelectric point obtained in the seventh step.

BRIEF DESCRIPTION OF THE DRAWINGS

FIG. 7A is a view schematically showing *Escherichia coli* in which the gene expressing the Fab' antibody having a uniform isoelectric point is incorporated.

FIG. 7B is a view schematically showing the Fab' antibody having a uniform isoelectric point which was produced by antibody induction with IPTG.

FIG. 7C is a view schematically showing the fluorescently labeled Fab' antibody having a uniform isoelectric point.

FIG. 7D is a view schematically showing the relation of migration time and fluorescence intensity obtained when electrophoresis is performed to the immune complex comprising the fluorescently labeled Fab' antibody having a uniform isoelectric point and the antigen.

FIG. 8A is a view schematically showing IgG antibody produced by a hybridoma.

FIG. 8B is a view schematically showing the F(ab')$_2$ antibody obtained by cutting IgG antibody produced by the hybridoma with a protease.

FIG. 8C is a view schematically showing the Fab' antibody obtained by reducing disulfide bonds by treating F(ab')$_2$ antibody with a reducing agent.

FIG. 8D is a view schematically showing the Fab' antibody in which one reactive thiol group is left by oxidation.

FIG. 8E is a view schematically showing the fluorescently labeled Fab' antibody.

FIG. 8F is a view schematically showing the elecrtophoretic image obtained by subjecting the fluorescently labeled Fab' antibody to isoelectric focusing.

FIG. 8G is a view schematically showing the relation of migration time and fluorescence intensity obtained when electrophoresis is performed to the immune complex comprising the fluorescently labeled Fab' antibody having a uniform isoelectric point which is obtained by isoelectric focusing, and the antigen.

BEST MODE FOR CARRYING OUT THE INVENTION

A method for quantitatively detecting an antigen of the present invention comprises (1) a first step of providing an Fab' antibody having a uniform isoelectric point, said antibody forming an immune complex with an antigen in an analytical sample and being modified by adding an amino acid sequence comprising a charged amino acid residue and by being labeled with a fluorescent dye, (2) a second step of mixing the Fab' antibody having a uniform isoelectric point with the analytical sample containing the antigen to obtain a mixture comprising the immune complex, (3) a third step of separating the mixture by performing electrophoresis in a carrier, (4) a fourth step of irradiating an excitation light which excites the fluorescent dye to the mixture separated in the third step to cause fluorescence in the immune complex, and (5) a fifth step of detecting the fluorescence.

Figure 1:
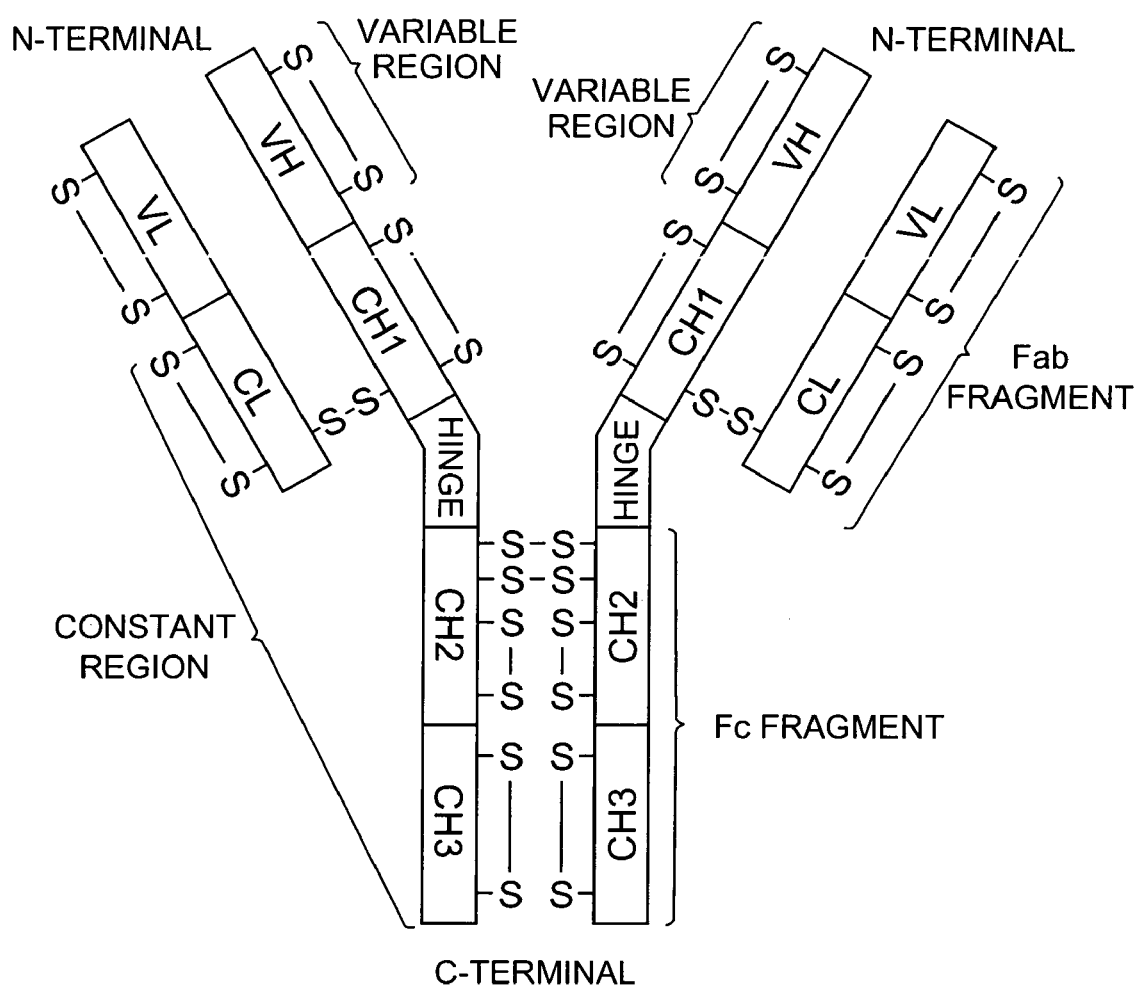
FIG. 1 is a view schematically showing human IgG1 antibody.

In the case of human IgG1 antibody, the antibody has the structure in which two polypeptide chains called L chain (light chain) and two polypeptide chains called H chain (heavy chain) makes a Y-shaped pair, as shown in FIG. 1. Fab' antibody is a fragment in which a hinge region or a part thereof is added to an Fab fragment. In the Fab' antibody, an Fd chain (H chain which is in an N-terminal side from a hinge region) consisting of a VH region and a CH1 region, and an L chain consisting of a VL region and a CL region are bonded by —S—S— bond.

Fab' antibody used in the present invention is used for detection of an antigen, therefore, it should form an immune complex by reacting specifically with an antigen included in an analytical sample. The type of the antigen for detection in the method for quantitative detection of the present invention is not limited in particular. Any antigens can be used insofar as they cause an antigen antibody reaction. The type of the analytical sample is also not limited in particular. Any analytical samples can be used insofar as they contain an antigen as an analyte.

An amino acid sequence comprising a charged amino acid residue is added to the Fab' antibody used in the present invention. The Fab' antibody which is modified by adding an amino acid sequence comprising a charged amino acid residue means, in the present invention, the Fab' antibody where an amino acid sequence comprising a positively or negatively charged amino acid residue is added to at least one site of the Fd chain, the L chain, or the hinge region (or a part thereof) in the Fab' antibody. The positively charged amino acid includes arginine, lysine, and the like. The negatively charged amino acid includes aspartic acid, glutamic acid, and the like. The site of the Fab' antibody modified with an amino acid sequence comprising a charged amino acid residue is not limited in particular. However, since the site in the VH region and the VL region of the Fab' antibody bonds with an antigen, the amino acid sequence comprising a charged amino acid residue is preferably added to the C-terminal side of the H chain or the L chain in the Fab' antibody in a viewpoint of antigen-antibody reactivity. More preferably, it is added adjacent to a C-terminal of an L chain. The number of amino acid residues in an amino acid sequence comprising a charged amino acid residue is not limited as long as it is 1 or more but the number is preferably 1 to 50. And, the number of charged amino acid residues in the amino acid sequence is also not limited as long as it is 1 or more but the number is preferably 1 to 30.

The method of adding the amino acid sequence comprising a charged amino acid residue to the Fab' antibody is not limited in particular. For example, as described below, polymerase chain reaction (PCR) is firstly performed using a primer for adding an amino acid sequence comprising a charged amino acid residue and using a gene expressing an Fab' antibody having a uniform isoelectric point as a template in order to obtain a gene expressing an Fab' antibody having a uniform isoelectric point modified by adding an amino acid sequence comprising a charged amino acid residue. Then, a host cell transformed with the resultant gene obtained in the above process is cultured. As another method, it is possible to combine an Fab' antibody having a uniform isoelectric point with an amino acid sequence comprising a charged amino acid residue which is prepared independently.

In addition to the modification by the amino acid sequence comprising a charged amino acid residue, the Fab' antibody used in the present invention is modified to show a uniform isoelectric point. The method of imparting a uniformity of an isoelectric point to the Fab' antibody is not limited in particular. However, preferably, a uniformity of an isoelectric point is given by changing an amide group-containing amino acid (asparagine and/or glutamine) in the CH1 region of the Fab' antibody into an amide group-non-containing amino acid except for cysteine using the genetic engineering, as described below.

The Fab' antibody used in the present invention is labeled with a fluorescent dye in addition to the modification by adding the amino acid sequence comprising a charge modified amino acid residue and by imparting a uniform isoelectric point. The example of the fluorescent dye includes rhodamine, fluorescein, cyanine, indocyanine, indocarbocyanine, pyronine, lucifer yellow, quinacrine, squarillium, coumarin, fluoroanthranilmaleimide, anthracene, and the like. In particular, it is preferred that rhodamine and/or cyanine is used. It is more preferred that rhodamine is used as a fluorescent dye. Rhodamine has a maximum absorption at 556 nm (molecular extinction coefficient: 93,000) in methanol and emits fluorescent light having a maximum of 576 nm. Regarding rhodamine, a reference can be made to Handbook of Fluorescent Probes and Research Chemicals, 5th Edition MOLECULAR PROBES, INC., 1992.

Further, in the present invention, an aromatic heterocyclic compound and a polycyclic aromatic hydrocarbon including anthracene, naphthalene, phenanthrene, quinoline, pyrene and perylene can be used as a fluorescent dye. Regarding such the fluorescent dye, a reference can be made to, for example, Fluorescence and Phosphorescence Analysis, authored by Yasuharu Nishikawa and Keizo Hiraki, published by Kyoritsu Shuppan, 1989.

When above-mentioned fluorescent dye and Fab' antibody are reacted, the labeling site with the fluorescent dye on the Fab' antibody is not limited in particular. However, the fluorescent dye is preferably bound to a SH group of cysteine residue of the Fab' antibody. And more preferably, it is bound to a SH group of cysteine residue which is not involved in binding with an L chain and exists in an amino acid sequence which adjoins to the C-terminal of the CH1 region of the Fab' antibody.

When above-mentioned fluorescent dye and Fab' antibody are reacted, the type of bond produced by the reaction is not limited in particular, however, preferably, it is at least one bond selected from the group consisting of a thioester bond, a dithioester bond, and a thioether bond. In this case, a fluorescent dye can be directly reacted with a functional group such as a SH group in an amino acid residue of the Fab' antibody, or can be reacted via a multifunctional compound having at least one functional group reactive with a functional group (for example, halogenated methyl group, active ester group, acid chloride group, anhydride group, maleimide group and the like) in a fluorescent dye and at least one functional group reactive with a SH group.

In the second step following the first step of the present invention, a mixture comprising an immune complex is obtained by mixing the above-mentioned Fab' antibody having a uniform isoelectric point which is modified by adding an amino acid sequence comprising a charged amino acid residue and is labeled with a fluorescent dye, with an analytical sample containing the above-mentioned antigen.

In the second step, a method for forming a complex is not particularly limited. For example, the complex can be formed by the following process. That is, a solution where the analytical sample containing an antigen is dissolved in the ultrapure water or the buffer solution at desired concentration is mixed with a solution where the Fab' antibody having a uniform isoelectric point, which is modified by adding an amino acid sequence comprising a charged amino acid residue and is labeled with a fluorescent dye (hereinafter, in some cases, it may be called a fluorescently labeled charged Fab' antibody having a uniform isoelectric point), is dissolved in the ultrapure water or the buffer solution at desired concentration. Then, the resultant mixture is kept from a low temperature (about 4° C.) to a room temperature (about 25° C.) for several minutes to several 10 minutes to obtain the complex. The mixed solution of the antigen and the fluorescently labeled charged Fab' antibody having a uniform isoelectric point is further dissolved in an electrophoresis carrier. The different type of an electrophoresis carrier is used depending on the type of electrophoresis. For example, when the isoelectric focusing is conducted, the electrophoresis carrier such as a slab gel, a polyacrylamide gel or the like is used for a migration. On the one hand, when the capillary isoelectric focusing is conducted, the ampholite carrier such as Pharmalyte (available from Amersham Pharmacia Biotech Co.) is used. In addition, when the capillary isoelectric focusing is conducted, hydroxypropyl methylcellulose or the like can be added further in order to prevent an electroosmotic flow or an adsorption of protein.

In the third step, electrophoresis of the mixture obtained in the second step is performed, and the mixture is separated.

The method for the electrophoresis in the third step is not particularly limited. Since detection accuracy is excellent, it is preferable to perform the isoelectric focusing. Moreover, since an immune complex can be detected even with a very small amount, use of the capillary electrophoresis is preferable. It is also possible to perform microcell electrophoresis or microchip electrophoresis. In the present invention, it is more preferable to use the capillary isoelectric focusing because it can detect an immune complex with high accuracy even with very small amount.

When the capillary electrophoresis is performed, the capillary typically has an inside diameter of from several micrometers to about 100 micrometers, an outside diameter of several 100 micrometers, and a length of from several 10 centimeters to 100 centimeters, and is composed of a soda lime glass or the like. These dimensions, especially length, are suitably selected depending on, for example, the type of an immune complex for measurement.

Voltage to be charged is not particularly limited. It can be selected suitably according to the type of electrophoresis, the type and concentration of an immune complex measured, the form and length of a migration carrier, the type of electrophoresis apparatus used, and etc.

In the fourth step, an excitation light which excites the fluorescent dye is irradiated to the mixture separated in the third step to cause fluorescence in the immune complex. The type of excitation light is not particularly limited. When rhodamine is used as a fluorescent dye, use of an argon laser, a semiconductor excitation YAG laser, and a helium neon laser, or the like is suitable.

In the fifth step, the fluorescence caused in the fourth step is detected. As a means for fluorescence detection, an optical detector that can perform fluorescence detection is used. For example, a densitometer (for example, Shimadzu 2 wave flying-spot scanning densitometer CS9300PC, available from Shimadzu Co.) is preferably used as an optical detector.

Fluorescence intensity is measured by an optical detector. Concentration of a detected complex can be quantified based on a relation between concentration and the fluorescence intensity for the fluorescent dye that is obtained prior to the measurement.

As explained above, since the antibody used in the present invention has a uniform isoelectric point, plural peaks observed by electrophoresis are ascribable to the ununiformity of an isoelectric point of the antigen. In addition, since the antibody used in the present invention is fluorescently labeled with a fluorescent dye or the like, detection can be done with high accuracy. Furthermore, since the antibody used in the present invention is modified by adding an amino acid sequence comprising a charged amino acid residue, the isoelectric point can be changed to a desired value while maintaining a uniformity of the isoelectric point by changing the type and/or the amount of introduction of the charged amino acid residue. Therefore, even when an isoelectric point of the antigen (analyte) is close to that of the antibody, the immune complex is detected at the migration time which is different from that of the excessive antigen an/or antibody. Then, analysis can be done with high accuracy.

It is not impossible to chemically modify the Fab' antibody used in the above-mentioned method by Shimura K and Karger B L in order to make the isoelectric point of the Fab' different from that of an antigen by imparting charges. However, since a functional group (for example, amino group) used for chemical modification is randomly distributed in the Fab' antibody, uniform modification is impossible. In addition, uniformity of the isoelectric point can be deteriorated by the modification. Therefore, it is impossible with the method by Shimura K and Karger B L to conduct an analysis with high accuracy when an isoelectric point of the antigen (analyte) is close to that of the fluorescently labeled antibody.

In the present invention, the fluorescently labeled charged Fab' antibody having a uniform isoelectric point which is used for a quantitative detection of the antibody is preferably produced by either of the first to fifth method of preparing based on the genetic engineering described below.

The first preparing method based on the genetic engineering comprises (1) a first step of providing an Fd chain gene encoding a VH region, a CH1 region, and an amino acid sequence which adjoins to a C-terminal of the CH1 region and comprises a cysteine residue which is not involved in binding with an L chain in an Fab' antibody, (2) a second step of site-specifically mutating in the Fd chain gene at least one codon encoding an amide group-containing amino acid residue in the CH1 region, into a codon encoding an amide group-non-containing amino acid residue except for cysteine to obtain a modified Fd chain gene, (3) a third step of linking the modified Fd chain gene and an L chain gene encoding an L chain of the Fab' antibody in the expressible state to obtain a gene expressing a modified Fab' antibody, (4) a fourth step of modifying the gene expressing a modified Fab' antibody to express an amino acid sequence comprising a charged amino acid residue adjacent to a C-terminal of the L chain to obtain a gene expressing a charge modified Fab' antibody, (5) a fifth step of transforming a host cell with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region, and (6) a sixth step of binding a fluorescent dye to the cysteine residue which is not involved in binding with an L chain in the Fab' antibody having a uniform isoelectric point obtained in the fifth step.

In the first step, the method of providing the Fd chain gene encoding the VH region, the CH1 region, and the amino acid sequence which adjoins to the C-terminal of the CH1 region and comprises a cysteine residue which is not involved in binding with the L chain in the Fab' antibody is not particularly limited. The gene can be obtained by a method described below, for example.

That is, after an animal is immunized with an antigen, a monoclonal antibody-producing cell (hybridoma) is prepared according to a method described in, for example, Antibodies: A Laboratory Manual, Chapter 6, Cold Spring Harbor Laboratory, Cold Spring Harbor, N.Y. 1988. The whole mRNA is extracted from this monoclonal antibody-producing cell according to a protocol described in, for example, BioMag mRNA purification kit (PerSeptive) and this mRNA is used to synthesize a single-stranded cDNA (for example, cDNA Synthesizing System Plus of Amersham Pharmacia Biotech Inc. can be used).

Then, a polymerase chain reaction (PCR) can be performed to obtain an Fd chain gene using this single-stranded cDNA as a template and using a DNA primer for isolating an Fd chain gene which is designed for introducing an amino acid sequence containing a cysteine residue which is not involved in binding with an L chain into a part adjacent to the C-terminal of the CH1 region. Regarding the DNA primer for isolating the Fd chain gene, a reference can be made to the base sequence of the nucleic acid of the variable region (V region) and the constant region (C region) which was classified by Kabat et al. (Sequences of Proteins of Immunological Interest 5th ed., Public Health Service, NIH, Washington D.C., 1991). For designing the primer for introducing the amino acid sequence containing a cysteine residue which is not involved in binding with an L chain into a part adjacent to a C-terminal of a CH1 region, a reference can be made to publications such as Hoogenboom H. R. et al. (Nucleic Acids Res. 1991 Aug. 11; 19(15): 4133–7) and Kang A. S. et al. (Methods (San Diego)(1991), 2(2), 111–18).

The number of amino acid residues of an amino acid sequence to be introduced into a part adjacent to the C-terminal of the CH1 region is not limited as long as it is 1 or more but the number is preferably 1 to 30. In addition, the number of cysteine residues in the amino acid sequence is not particularly limited but the number is preferably 1 to 3 and, more preferably 1.

In addition, upon preparation of a monoclonal antibody-producing cell in the present invention, the kind of an antigen immunizing an animal and the kind of an animal to be immunized with the antigen are not particularly limited. As the antibody gene, those derived from mouse, rat and rabbit can be used. The class and subclass of the antibody are not particularly limited but it is preferred that the sequence which constitutes an IgG antibody is used due to a larger proportion in the all antibodies.

In the second step, at least one codon encoding an amide group-containing amino acid residue of the CH1 region is site-specifically mutated into a codon encoding an amide group-non-containing amino acid residue except cysteine in the Fd chain gene and this mutating method is not particularly limited. For example, site-specific mutagenesis that is widely used as a method for mutating a nucleotide sequence of a gene can be applied thereto. Regarding the site-specific mutagenesis, for example, a reference can be made to Sambrook et al., Molecular Cloning; A Laboratory Manual 2nd Edition, 15.2–15.113, Cold Spring Harbor Press, Cold Spring Harbor, N.Y., 1989.

The aforementioned site-specific mutagenesis is preferably conducted by a polymerase chain reaction using a primer for amplifying a CH1 region which substitutes at least one amide group-containing amino acid residue of a CH1 region with an amide group-non containing amino acid residue except for cysteine. This primer for amplifying a CH1 region has a base sequence complementary to the base sequence encoding the region containing at least one amide group-containing amino acid residue in the CH1 region of the Fd chain. However, in the base sequence of the primer, at least one codon complementary to a codon encoding the amide group-containing amino acid residue is substituted with a codon complementary to a codon encoding an amide group-non containing amino acid except for cysteine.

The aforementioned "amide group-containing amino acid residue" means an amino acid residue having an amide group on its side chain. An asparagine residue and a glutamine residue are the examples of such amino acid residue. In the second step, at least one codon encoding these amino acid residues is site-specifically mutated into a codon encoding an amide group-non-containing amino acid residue except for cysteine. Here, "an amide group-non-containing amino acid residue" means an amino acid residue having no amide group on its side chain. Either natural amino acid residue or unnatural amino acid residue can be used as the amide group-non-containing amino acid residue. The example of the natural amino acid residue includes glycine residue, alanine residue, valine residue, leucine residue, isoleucine residue, serine residue, threonine residue, methionine residue, aspartic acid residue, glutamic acid residue, lysine residue, arginine residue, phenylalanine residue, tyrosine residue, proline residue, histidine residue, and tryprophan residue. As the unnatural amino acid, there are an amino acid in which a side chain of the natural amino acid is substituted with an aromatic ring or the like, an artificial amino acid such as a chemically synthesized amino acid and the like.

In the present invention, at least one amide group-containing amino acid residue is preferably mutated into an amide group-non-containing amino acid residue. When cysteine residues are introduced as the amide group-non-containing amino acid residue by the mutation, the resultant amino acid sequence, which contains a lot of cystein residues that are not involved in binding with the L chain, may show a uniform isoelectric point. However, when a fluorescent dye is bound to the cysteine residues introduced, an isoelectric point becomes ununiform because the number and a position of the fluorescent dye become indefinite. For this reason, in the present invention, it is not preferred to use a cysteine residue as an amide group-non-containing amino acid residue.

In the present invention, it is preferred that the aforementioned amide group-non-containing amino acid residue is an aspartic acid residue, a glutamic acid residue, a glycine residue or a serine residue because of the excellent uniformity of isoelectric point of the resultant Fab' antibody having a uniform isoelectric point. In addition, it is preferred that an Fab' antibody used has an asparagine residue at the 162nd position in the H chain according to the Kabat numbering system and this asparagine residue is site-specifically mutated into an amide group-non-containing amino acid residue except for cysteine. In the present invention, it is more preferred that an asparagine residue at the 162nd position in the H chain according to the Kabat numbering system be mutated into an aspartic acid residue. Example of the Fab' antibody having an asparagine residue at the 162nd position in the H chain according to the Kabat numbering system includes mouse IgG antibody-derived Fab' antibody and human IgG antibody-derived Fab' antibody. Although a variety of subclasses are present in mouse IgG antibody and human IgG antibody, Fab' antibodies derived from these antibodies have an asparagine residue at the 162nd position in the H chain according to the Kabat numbering system even in a different subclass. Here, "amino acid residue at the 162nd position in the H chain according to the Kabat numbering system" means that the amino acid residue in the H chain (Fd chain) of the Fab' antibody located at "162nd" position based on the method described in Sequence of Proteins of Immunological Interest (Paperback 5th edition (September 1992)) by Elvin A. Kabat. The 162nd amino acid residue in the H chain according to the Kabat numbering system is in the CH1 region of the Fd chain.

The modified Fd chain gene obtained by the aforementioned second step is bound to the L chain gene encoding the L chain of an Fab' antibody in the expressible state in the third step. This can afford a gene expressing a modified Fab' antibody.

The L chain gene encoding the L chain of the Fab' antibody can be obtained according to the similar manner to that for obtaining the Fd gene in the first step. That is, after an animal is immunized with an antigen, a monoclonal antibody-producing cell (hybridoma) is prepared. The whole mRNA is extracted from this monoclonal antibody-producing cell, and a single-stranded cDNA is synthesized using this mRNA. Then, PCR is performed using this cDNA as a template and using a DNA primer for isolating an L chain gene. In the present invention, the L chain gene can be obtained at the same time with isolating the Fd chain gene in the first step. In this case, PCR may be performed using a DNA primer for isolating the Fd chain gene and the DNA primer for isolating the L chain gene and using the cDNA as a template in the first step.

In the present invention, in addition to site-specific mutation of at least one codon encoding an amide group-containing amino acid residue of the CH1 region in the Fd chain gene into a codon encoding an amide group-non-containing amino acid residue except for cysteine, at least one codon encoding an amide group-containing amino acid residue (asparagine residue and/or glutamine residue) of the CL region in the L chain gene obtained as described above may be site-specifically mutated into an amide group-non-containing amino acid residue except for cysteine. This site-specific mutation can be performed before or after binding with the modified Fd chain gene in the expressible state. In this case, it is preferred that the Fab' antibody used has an asparagine residue at least one of the 157th, 161st, or 190th positions of the L chain (all present in a CH region) according to the Kabat numbering system. It is preferred that at least one asparagine residue is site-specifically mutated into an amide group-non-containing amino acid residue except for cysteine. In particular, it is preferred that an asparagine residue at the 161st position in the L chain according to the Kabat numbering system is site-specifically mutated into an amide group-non-containing amino acid residue except for cysteine. It is more preferred that an asparagine residue at the 161st position in the L chain is mutated into an aspartic acid residue. Regarding the site-specific mutating method, a reference can be made to Sambrook et al., Molecular Cloning: A Laboratory Manual 2nd Edition, 15.2–15.113, Cold Spring Harbor Press, Cold Spring Harbor, N.Y., 1989 as described above. As in the case of the CH1 region, it is preferred that the site-specific mutation of the CL region is performed by a polymerase chain reaction using a primer for amplifying the CL region which substitutes at least one amide group-containing amino acid residue of the CL region with an amide group-non-containing amino acid residue except for cysteine.

By binding above-obtained L chain gene and the aforementioned modified Fd chain gene via a linker base sequence or the like, a gene expressing a modified Fab' antibody including above genes can be obtained. More particularly, the L chain gene, the modified Fd chain gene and the linker base sequence are purified using, for example, low melting point agarose gel electrophoresis and purified genes are digested by an appropriate restriction enzyme. Then, digested genes are ligated so that the modified Fd chain gene, the linker base sequence and the L chain gene are arranged in this order. The linker base sequence can be obtained using a template plasmid vector for expressing a protein and using a DNA primer for isolating the linker base sequence.

In the fourth step following the third step, the gene expressing a modified Fab' antibody is modified to express an amino acid sequence comprising a charged amino acid residue adjacent to a C-terminal of the L chain. This can afford a gene expressing a charge modified Fab' antibody. The method for this modification is not particularly limited. For example, it can be obtained by performing PCR using the gene expressing a modified Fab' antibody as a template and using a primer for adding an amino acid sequence comprising a charged amino acid residue adjacent to the C-terminal of the L chain.

In the fifth step, a host cell is transformed with the gene expressing a charge modified Fab' antibody and culturing the resultant transformant. This can afford an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region That is, the gene expressing a charge modified Fab' antibody obtained in the fourth step is ligated to an appropriate vector and this is introduced into a host cell to transform it. As a vector, a variety of known vectors such as a vector derived from a plasmid, a phage, a cosmid or the like can be used. As a host cell, for example, there are procaryotic cell, that is, *Escherichia coli* (SOLR, JM109, XL1-BlueMRF', BL21 (DE3), HB2151), *Bacillus subtilis*, *Bacillus brevis*, and eukaryotic cell, that is, yeast, and cell derived from an animal (HB101, CHO cell, COS cell, COP-5, C127, 3T3 cell and the like). As a host cell, it is preferred that a protease-non-producing bacteria is used from a viewpoint of degradation resistance of the Fab' antibody having a uniform isoelectric point.

As the method of introducing the vector into the host cell, known methods including a microinjection method, electropolation method and the like can be applied. The method for culturing the transformant is not particularly limited and a medium suitable for culturing the transformant may be selected. In addition, as the method for extracting the Fab' antibody having a uniform isoelectric point produced by culturing a transformant, cell homogenization method, lysis of cell wall using a surfactant such as SDS or an enzyme, ultrasonicating method, and the like can be adopted. The method for purifying the extracted Fab' antibody having a uniform isoelectric point includes centrifugation such as ultracentrifugation and gradient centrifugation, column-separation utilizing an affinity column and the like, gel-separation utilizing polyacrylamide gel, and the like.

In the sixth step, a fluorescent dye is bound to the cysteine residue which is not involved in binding with an L chain in the Fab' antibody having a uniform isoelectric point obtained in the fifth step.

Here, the fluorescent dye described above can be used. The type of bond produced by the reaction is preferably at least one bond selected from the group consisting of a thioester bond, a dithioester bond, and a thioether bond. In this case, the fluorescent dye can be directly reacted with a functional group such as a SH group in the amino acid residue of the Fab' antibody, or can be reacted via a multifunctional compound having at least one functional group reactive with a functional group in the fluorescent dye and at least one functional group reactive with a SH group.

In the first preparing method based on the genetic engineering described above, after the modified Fd chain gene and the L chain gene are linked in the expressible state in the third step, the linked gene is modified in the fourth step to express an amino acid sequence comprising a charged amino acid residue adjacent to a C-terminal of the L chain. As another preparing method, the L chain gene can be modified to express an amino acid sequence comprising a charged amino acid residue adjacent to the C-terminal of the L chain before the modified Fd chain gene and the L chain gene are linked. This preparing method is called the second preparing method based on the genetic engineering, hereinafter.

That is, in the second preparing method based on the genetic engineering, in the first step there is provided an Fd chain gene encoding a VH region, a CH1 region, and an amino acid sequence which adjoins to a C-terminal of the CH1 region and comprises a cysteine residue which is not involved in binding with an L chain in an Fab' antibody. In the second step, at least one codon encoding an amide group-containing amino acid residue in the CH1 region of the Fd chain gene is site-specifically mutated into a codon encoding an amide group-non-containing amino acid residue except for cysteine to obtain a modified Fd chain gene.

This first step and second step can be performed similarly to the first step and second step of the first preparing method based on the genetic engineering. The preferred number of an amino acid residue in the amino acid sequence introduced adjacent to the C-terminal of the CH1 region, the preferred number of a cysteine residue in the amino acid sequence, and the type of antigen and antibody are the same as those described in the first preparing method based on the genetic engineering. The kind of a amide group-containing amino acid residue, the kind of an amide group-non-containing amino acid residue, and the preferred amino acid residue thereof are the same as those described in the second step of the first preparing method based on the genetic engineering.

In the third step, an L chain gene encoding an L chain of the Fab' antibody is provided. The L chain gene can be obtained according to the similar manner to that described in the third step of the first preparing method based on the genetic engineering. In addition, the L chain gene can be also obtained at the same time with isolating the Fd chain gene in the first step.

In the fourth step following the third step, the L chain gene is modified to express an amino acid sequence comprising a charged amino acid residue adjacent to the C-terminal of the L chain. This can afford a charge modified L chain gene. The modification in this step can be done according to the similar manner to that described in the fourth step of the first preparing method based on the genetic engineering. Here, at least one codon encoding an amide group-containing amino acid residue of the CL region in the L chain gene may be site-specifically mutated into a codon encoding an amide group-non-containing amino acid residue except for cysteine. This site-specific mutation can be performed in the third step.

In the fifth step, the modified Fd chain gene and the charge modified L chain gene are liked in the expressible state. This can afford a gene expressing a charge modified Fab' antibody. Conditions for linking in the expressible state are the same as those described in the third step of the first preparing method based on the genetic engineering.

Subsequently, in the sixth step, a host cell is transformed with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region. In the seventh step, a fluorescent dye is bound to the cysteine residue which is not involved in binding with the L chain in the Fab' antibody having a uniform isoelectric point. The sixth and seventh steps can be performed similarly to the fifth and sixth steps of the above-mentioned first preparing method based on the genetic engineering.

In the first and second preparing methods based on the genetic engineering described above, after the Fd chain gene is site-specifically mutated, the resultant gene is linked with an L chain gene. As the third preparing method based on the genetic engineering, after the Fd chain gene and the L chain gene are linked, the Fd chain gene can be site-specifically mutated.

That is, in the first step, there is provided an Fd chain gene encoding a VH region, a CH1 region, and an amino acid sequence which adjoins to the C-terminal of the CH1 region and comprises a cysteine residue which is not involved in binding with an L chain in an Fab' antibody, and provided an L chain gene encoding the L chain of the Fab' antibody. In the second step following the first step, the Fd chain gene and the L chain gene are linked in the expressible state to obtain a gene expressing an Fab' antibody. In this case, the Fd chain gene can be obtained according to the similar manner to that described in the first step of the first preparing method based on the genetic engineering. The L chain gene can be obtained according to the similar manner to that described in the third step of the first preparing method based on the genetic engineering. Linking the Fd chain gene and the L chain gene in the expressible state can be done according to the similar manner to that described in the third step of the first preparing method based on the genetic engineering. That is, a linker base sequence is obtained using a template plasmid vector for expressing a protein and using a DNA primer for isolating a linker base sequence. This linker base sequence, the Fd chain gene and the L chain gene are ligated in the expressible state. The preferred number of an amino acid residue in the amino acid sequence introduced adjacent to the C-terminal of the CH1 region, and the suitable number of a cysteine residue in the amino acid sequence are the same as those described in the first preparing method based on the genetic engineering.

In the third step, the gene expressing an Fab' antibody is modified to express an amino acid sequence comprising a charged amino acid residue adjacent to the C-terminal of the L chain, and in the gene expressing an Fab' antibody at least one codon encoding an amide group-containing amino acid residue in the CH1 region is site-specifically mutated into a codon encoding an amide group-non-containing amino acid residue except for cysteine. This can afford a gene expressing a charge modified Fab' antibody.

In this case, there is no limitation of the order of the modifications described above—modifation to express an amino acid sequence comprising a charged amino acid residue adjacent to the C-terminal of the L chain, and site-specific mutation of at least one codon encoding an amide group-containing amino acid residue in the CH1 region into a codon encoding an amide group-non-containing amino acid residue except for cysteine.

For example, firstly, the gene expressing an Fab' antibody is modified to express an amino acid sequence comprising a charged amino acid residue adjacent to a C-terminal of the L chain to obtain a gene expressing an Fab' antibody having a charged amino acid. Then, at least one codon encoding an amide group-containing amino acid residue in the CH1 region in the gene expressing an Fab' antibody having a charged amino acid is site-specifically mutated into a codon encoding an amide group-non-containing amino acid residue except for cysteine to obtain a gene expressing a charge modified Fab' antibody. Alternatively, firstly, at least one codon encoding an amide group-containing amino acid residue in the gene expressing an Fab' antibody is site-specifically mutated into a codon encoding an amide group-non-containing amino acid residue except for cysteine to obtain a gene expressing a modified Fab' antibody. Then, the gene expressing a modified Fab' antibody is modified to express an amino acid sequence comprising a charged amino acid residue adjacent to the C-terminal of the L chain to obtain a gene expressing a charge modified Fab' antibody.

Site-specific mutation in the third step can be performed according to the similar manner to that described in the second step of the first preparing method based on the genetic engineering. The preferred amide group-containing amino acid, the preferred amide group-non-containing amino acid, and the preferred amino acid thereof are the same as those described in the first preparing method based on the genetic engineering. Modification to express an amino acid sequence comprising a charged amino acid residue adjacent to the C-terminal of the L chain can be done according to the similar manner to that described in the fourth step of the first preparing method based on the genetic engineering. Here, at least one codon encoding an amide group-containing amino acid residue of the CL region in the gene expressing Fab' antibody may be site-specifically mutated into a codon encoding an amide group-non-containing amino acid residue except for cysteine. This site-specific mutation can be performed in the first step.

In the fourth step, a host cell is transformed with the gene expressing a charge modified Fab' antibody and culturing the resultant transformant to obtain an Fab' antibody having a uniform isoelectric point, the Fab' antibody being modified by adding an amino acid sequence comprising a charged amino acid residue adjacent to the C-terminal of the L chain, and by adding an amino acid sequence comprising a cysteine residue which is not involved in binding with an L chain adjacent to the C-terminal of the CH1 region. The kind of a host cell, the kind of a vector which is introduced into a host cell, the method for introducing a vector into a host cell and the method for extracting an Fab' antibody having a uniform isoelectric point produced by culturing a transformant are the same as those described in the fifth step of the first preparing method based on the genetic engineering.

In the fifth step, a fluorescent dye is bound to the cysteine residue which is not involved in binding with the L chain in the Fab' antibody having a uniform isoelectric point obtained in the fourth step. The kind of fluorescent dye, the preferred fluorescent dye, and the kind of bonding between cysteine residue and fluorescent dye are the same as those described in the sixth step of the first preparing method based on the genetic engineering.

In addition to the above-mentioned first to third preparing method based on the genetic engineering, the fourth preparing method based on the genetic engineering described below is also applicable.

That is, in the first step, there is provided a CH1 gene encoding a CH1 region and an amino acid sequence which adjoins to the C-terminal of the CH1 region and comprises a cysteine residue which is not involved in binding with the L chain in the first Fab' antibody, and a CL gene encoding the CL region of the first Fab' antibody.

The CH1 gene in the first step can be obtained, for example, by extracting the whole mRNA from a monoclonal antibody-producing cell (hybridoma), synthesizing a single-stranded cDNA using this mRNA, and performing PCR using this cDNA as a template and using a primer to introduce an amino acid sequence comprising a cysteine residue which is not involved in binding with the L chain into a part adjacent to the C-terminal of the CH1 region. The CH1 gene may be any one that encodes a region containing the CH1 region. The CH1 gene can be the one encoding only the CH1 region or the one encoding the CH1 region and the VH region. In addition, the CH1 gene may be the one encoding the CH1 region and the hinge region, or the one encoding the CH1 region, the VH region and the hinge region. Regarding the VH region and the hinge region, at least part thereof may be encoded. The preferred number of an amino acid residue in the amino acid sequence introduced adjacent to the C-terminal of the CH1 region, the preferred number of a cysteine residue in the amino acid sequence, and the type of antigen and antibody are the same as those described in the first preparing method based on the genetic engineering.

The CL gene in the first step can be obtained at the same time or independently with obtaining the above-mentioned CH1 gene. It can be obtained by performing PCR using a single-stranded cDNA, which is obtained from a mRNA derived from a monoclonal antibody-producing cell, as a template, and using a primer for isolating a CL chain gene Here, at least one codon encoding an amide group-containing amino acid residue in the CL gene obtained in the first step may be site-specifically mutated into a codon encoding an amide group-non-containing amino acid residue except for cysteine.

In the second step, in the CH1 gene, at least one codon encoding an amide group-containing amino acid residue in the CH1 region is site-specifically mutated into a codon encoding an amide group-non-containing amino acid residue except for cysteine. This can afford a modified CH1 gene.

This site-specific mutation can be done according to the similar manner to that described in the second step of the first preparing method based on the genetic engineering. The kind of a amide group-containing amino acid residue, the kind of an amide group-non-containing amino acid residue, and the preferred amino acid residue thereof are the same as those described in the first preparing method based on the genetic engineering.

Subsequently, in the third step, the modified CH1 gene is cut with a restriction enzyme to obtain a gene fragment encoding the CH1 region. The restriction enzyme used herein is not particularly limited. The example of the restriction enzyme includes BamHI and BglI.

In the fourth step, there is provided a VH gene encoding the VH region of the second Fab' antibody and a VL gene encoding the VL region of the second Fab' antibody. Here, the VH gene and the VL gene of the second Fab' antibody can be obtained by the following process, for example. That is, a single-stranded cDNA is synthesized using the mRNA of the antibody from which the second Fab' antibody is derived, then, PCR is performed using the cDNA as a template and using a DNA primer for isolating the VH gene and the VL gene. The second Fab' antibody may be the same as or different from the first Fab' antibody in terms of the class and the subclass. In addition, the animal species from which the second Fab' antibody is derived may be the same as or different from those of the first Fab' antibody. For example, the second Fab' antibody may be human IgG antibody and the first Fab' antibody may be mouse IgG antibody.

In the fifth step, the gene fragment, the CL gene, the VH gene and the VL gene are linked in the expressible state to obtain a gene expressing a modified Fab' antibody. Linking in the expressible state can be performed according to the similar manner to that described in third step of the first preparing method based on the genetic engineering.

In the sixth step, the gene expressing a modified Fab' antibody is modified to express an amino acid sequence comprising a charged amino acid residue adjacent to the C-terminal of the CL region. This can afford a gene expressing a charge modified Fab' antibody. Modification in the sixth step can be done according to the similar manner to that described in fourth step of the first preparing method based on the genetic engineering.

Subsequently, in the seventh step, a host cell is transformed with the gene expressing a charge modified Fab' antibody and the resultant transformant is cultured to obtain an Fab' antibody having a uniform isoelectric point. In the Fab' antibody having a uniform isoelectric point obtained in the seventh step, an amino acid sequence comprising a charged amino acid residue is added adjacent to the C-terminal of the L chain, and an amino acid sequence comprising a cysteine residue which is not involved in binding with an L chain is added adjacent to the C-terminal of the CH1 region.

The kind of a host cell, the kind of a vector to be introduced into a host cell, the method for introducing the vector into the host cell, and the method for extracting an Fab' antibody having a uniform isoelectric point produced by culturing the transformant are the same as those described in the fifth step of the first preparing method based on the genetic engineering.

In the eighth step, a fluorescent dye is bound to the cysteine residue which is not involved in binding with the L chain in the Fab' antibody having a uniform isoelectric point obtained in the seventh step. The kind of fluorescent dye, the preferred fluorescent dye, and the kind of bonding between the cysteine residue and the fluorescent dye are the same as those described in the sixth step of the first preparing method based on the genetic engineering.

In the fourth preparing method based on the genetic engineering described above, the gene fragment of the modified CH1 gene, the CL gene, the VH gene and the VL gene in the expressible state are linked in the fifth step, then, the linked gene is modified to express an amino acid sequence comprising a charged amino acid residue adjacent to the C-terminal of the CL region in the sixth step. As another preparing method, the CL gene can be modified to express an amino acid sequence comprising a charged amino acid residue adjacent to the C-terminal of the L chain before the CL gene is linked with other genes (or a gene fragment). This preparing method is called the fifth preparing method based on the genetic engineering, hereinafter.

That is, in the fifth preparing method based on the genetic engineering, there is provided in the first step a CH1 gene encoding a CH1 region and an amino acid sequence which adjoins to a C-terminal of the CH1 region and comprises a cysteine residue which is not involved in binding with an L chain in a first Fab' antibody, and a CL gene encoding a CL region of the first Fab' antibody. In the second step, at least one codon encoding an amide group-containing amino acid residue in the CH1 region is site-specifically mutatated into a codon encoding an amide group-non-containing amino acid residue except for cysteine to obtain a modified CH1 gene. Then, in the third step, the modified CH1 gene is cut with a restriction enzyme to obtain a gene fragment encoding the CH1 region.

The first to third steps of the fifth preparing method based on the genetic engineering can be performed according to the similar manner to those described in the first to third steps of the fourth preparing method based on the genetic engineering. Here, at least one codon encoding an amide group-containing amino acid residue in the CL gene obtained in the first step may be site-specifically mutated into a codon encoding an amide group-non-containing amino acid residue except for cysteine.

Subsequently, in the fourth step, the CL gene is modified to express an amino acid sequence comprising a charged amino acid residue adjacent to the C-terminal of the CL region to obtain a charge modified CL gene. Modification in the fourth step can be done according to the similar manner to that described in fourth step of the first preparing method based on the genetic engineering. The fourth step can be performed before the second step.

Subsequently, in the fifth step, there is provided a VH gene encoding the VH region of the second Fab' antibody and a VL gene encoding the VL region of the second Fab' antibody. In the sixth step, the gene fragment, the charge modified CL gene, the VH gene and the VL gene are linked in the expressible state to obtain a gene expressing a charge modified Fab' antibody.

The step for providing a VH gene and a VL gene can be performed in the similar manner to that described in the fourth step of the fourth preparing method based on the genetic engineering. Linking in the expressible state can be performed according to the similar manner to that described in third step of the first preparing method based on the genetic engineering.

Subsequently, in the seventh step, a host cell is transformed with the gene expressing a charge modified Fab' antibody and the resultant transformant is cultured to obtain an Fab' antibody having a uniform isoelectric point. In the Fab' antibody having a uniform isoelectric point obtained in the seventh step, an amino acid sequence comprising a charged amino acid residue is added adjacent to the C-terminal of the L chain, and an amino acid sequence comprising a cysteine residue which is not involved in binding with an L chain is added adjacent to the C-terminal of the CH1 region The kind of a host cell, the kind of a vector to be introduced into a host cell, the method for introducing the vector into the host cell and the method for extracting an Fab' antibody having a uniform isoelectric point produced by culturing a transformant are the same as those described in the fifth step of the first preparing method based on the genetic engineering.

In the eighth step, a fluorescent dye is bound to the cysteine residue which is not involved in binding with an L chain in the Fab' antibody having a uniform isoelectric point obtained in the seventh step. The kind of fluorescent dye, the preferred fluorescent dye, and the kind of bonding between the cysteine residue and the fluorescent dye are the same as those described in the sixth step of the first preparing method based on the genetic engineering.

EXAMPLES

The present invention will be explained in detail by way of preferred Example but is not limited thereto. In addition, in Example, unless indicated for genetic-engineering procedures, the procedures were according to Sambrook et al., Molecular Cloning: A Laboratory Manual 2nd Edition, Cold Spring Harbor Press, Cold Spring Harbor, N.Y., 1989. In addition, reagents which are not particularly indicated were purchased from Takara Shuzo or Wako Pure Chemical Industries Ltd. for use.

Abbreviations used in this Example are as follows;

PCR: polymerase chain reaction (Gene amplifying method)

BAP: bacterial alkaline phosphatase

IPTG: isopropyl-$\beta$-D-thiogalactopyranoside

PBS: phosphate buffered saline

BSA: bovine serum albumin (1) Establishment of a Hybridoma

A hybridoma producing anti-human alpha-1-antitrypsin antibody was made using human alpha-1-antitrypsin (manufactured by Carbiochem-Noviochem) as an immunization antigen according to the following method:

A BALB/c mouse was immunized four times with the above immunogen, spleen cells were taken, cell fusion was performed using a cultured mouse marrow cell (x63Ag8) and polyethylene glycol and cloning was performed. The binding activity of the immunogen with the antibody in the culture supernatant of the resultant clone was measured by the enzyme-antibody method A clone that was considered to be positively reactive was further confirmed using the indirect fluorescent method. Then, nine kinds of hybridomas that produce the alpha-1-antitrypsin antibody were established. The antibodies produced by these hybridomas are the ones that bind to the human alpha-1-antitrypsin. For preparing the Fd gene and the L chain ($\kappa$ chain) gene of the Fab' antibody having a uniform isoelectric point described below, these cells that produce anti-human alpha-1-antitrypsin antibody having the anti-alpha-1-antitrypsin activity were used.

A gene expressing anti-human alpha-1-antitrypsin Fab' antibody was isolated from a hybridoma producing an IgG1 antibody against human alpha-1-antitrypsin as follows:

That is, the total RNA was extracted from the cells producing the anti-human alpha-1-antitrypsin Fab' antibody according to the protocol of BioMag mRNA purification kit (PerSeptive), and a single-stranded cDNA was synthesized using cDNA Synthesis System Plus (manufactured by Amersham Pharmacia Biotech Inc.). Polymerase chain reaction (PCR) was performed using the aforementioned cDNA as a template and using a DNA primer for isolating the Fd chain gene and a DNA primer for isolating the L chain gene, which were synthesized based on the base sequence of the variable region (V region) and the constant region (C region) classified by Kabat et al. (Sequences of Proteins of Immunological Interest, 5$^{th}$ ed., Public Health Service, NIH, Washington D.C., 1991). Here, for designing a primer, reference was made to Hoogenboom H. R. et al. (Nucleic Acids Res., 1991, Aug. 11:19 (15): 4133–7), and Kang A. S. et al. (Methods (San Diego) (1991), 2 (2), 111–18).

In order to express an antibody which binds to the human alpha-1-antitrypsin as an Fab' antibody, a DNA primer was designed so that both the heavy chain (H chain) and the light chain (L chain) contain constant region. That is, a 5' primer (F5-1 primer shown below) and a 3' primer (F3 primer shown below) were designed as a DNA primer for isolating the Fd chain gene, and a 5' primer (Kapper5 primer shown below) and a 3' primer (K3-1 primer shown below) were designed as a DNA primer for isolating the L chain gene.

The F5-1 primer which is a 5' primer for isolating the Fd chain gene had the sequence shown below (SEQ ID NO: 1) and the F3 primer which is a 3, primer for isolating the Fd chain gene had the sequence shown below (SEQ ID NO: 2). In the following sequences, 5, and 3' mean a 5' side and a 3, side, respectively. S indicates C or G, M indicates A or C, R indicates A or G, and W indicates A or T.

```
F5-1 primer (SEQ ID NO: 1)
5' SAGGTSMARCTGCAGSAGTCWGG 3'

F3 primer (SEQ ID NO: 2)
5' GCGTCATCTAGAACAACCACAATCCCTGGGCACA 3'
```

The F3 primer was designed so that a base sequence comprising a cysteine residue which is not involved in disulfide bond with the L chain can be introduced into a part adjacent to the C-terminal of the CH1 region, and in order to ligate to the L chain via a linker, it was designed so that a Xba I site is added thereto.

The Kapper5 primer which is a 5' primer for isolating the L chain gene had the sequence shown below (SEQ ID NO: 3) and the K3-1 primer which is a 3' primer for isolating the L chain gene had the sequence shown below (SEQ ID NO: 4). W indicates A or T, S indicates C or G, B indicates a base other than A, N indicates A, T, G or C, M indicates A or C, D indicates a base other than C, Y indicates C or T, H indicates a base other than G, respectively.

```
Kapper5 primer (SEQ ID NO: 3):
5' CCAGWTSYGAGCTCSWBNTSACNCAGNMDYCH 3'

K5-1 primer (SEQ ID NO: 4):
5' ACACTCATTCCTGTTGAAGCT 3'
```

PCR was performed under the conditions of 30 cycles of 1 minute at 94° C., 1 minute at 55° C., and 1 minute at 72° C. After PCR, DNA fragments of the resultant Fd chain, the linker base sequence and the L chain (κ chain) were purified by agarose gel electrophoresis, the Fd chain was digested with XbaI, the linker base sequence with XbaI and SacI, and the L chain (κ chain) with SacI. Respective DNA fragments were ligated so that the Fd chain, the linker base sequence and the L chain (κ chain) were arranged in this order. The ligation product was extracted with phenol/chloroform/isoamylalcohol (25/24/1). This was dissolved in TE buffer, and PCR was performed again with a primer designed so that a SfiI site is added to a 5' side of the Fd chain and a NotI site is added to a 3' side of the L chain. PCR was performed for 25 cycles of 1 minute at 94° C., 1 minute at 55° C. and 2.5 minutes at 72° C.

Figure 2A:
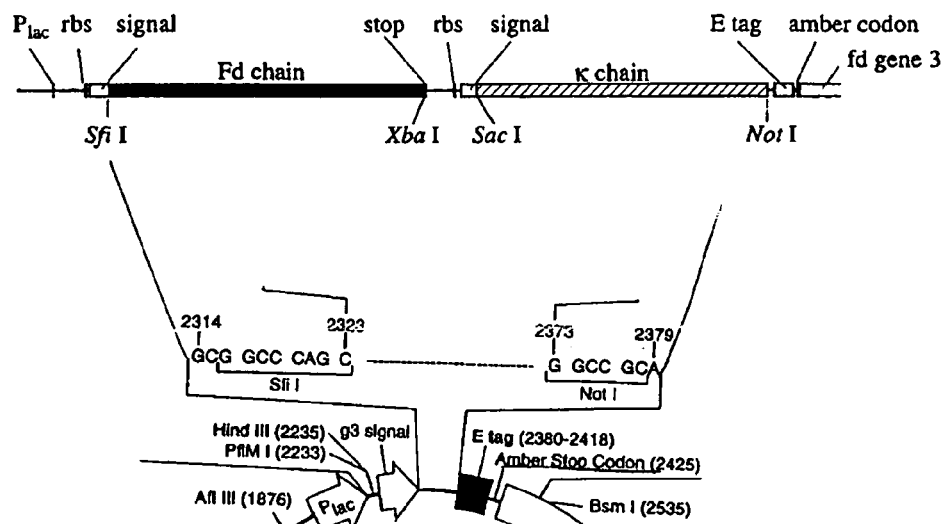
FIG. 2A is a constituent view of the gene expressing the Fab' antibody having a uniform isoelectric point.
Figure 2B:
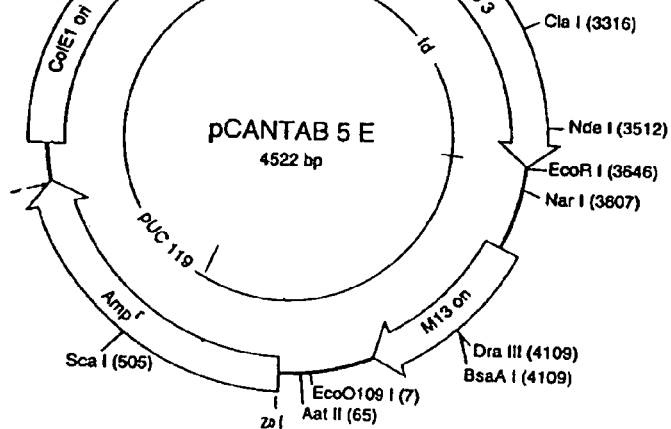
FIG. 2B is a view showing the pCANTAB5E plasmid vector to which the gene expressing the Fab' antibody having a uniform isoelectric point is introduced.

After the resultant PCR amplified-product was purified, it was digested with SfiI (20 U per reaction) at 50° C. for 4 hours and with NotI (40 U per reaction) at 37° C. for 4 hours. This was cloned into the pCANTAB5E plasmid vector (manufactured by Amersham Pharmacia Biotech Inc.) (see FIGS. 2A and B). The pCANTAB plasmid vector secretes a protein derived from the gene outside a periplasm of *Escherichia coli* and it contains a signal peptide which expresses a gene incorporated into a vector. The procedures and methods for constructing a vector which are conventionally used in the genetic-engineering field can be used.

(3) Transformation for Expressing Anti-Human Alpha-1-Anititrypsin Fab' Antibody

The plasmid expressing an anti-human alpha-1-anititrypsin Fab' antibody, that was made by cloning a gene expressing an anti-human alpha-1-anititrypsin Fab' antibody was cloned into the pCANTAB5E plasmid vector, was transformed into the commercially available *Escherichia coli* HB2151 (manufactured by Amersham Pharmacia Biotech Inc.). The *Escherichia coli* HB2151 was made competent according to the protocol of Expression Module/Recombinant Pharge Antibody System (manufactured by Amersham Pharmacia Biotech Inc.). The transformed *Escherichia coli* HB2151 was seeded on the SOBAG medium and incubated at 30° C. overnight. Colony lift assay was performed on the produced colony according to the protocol of HRP/Anti-E tag Conjugate (manufactured by Amersham Pharmacia Biotech Inc.) to screen bacteria expressing Fab' antibody which causes an antigen-antibody reaction against the human alpha-1-anititrypsin.

A plurality of screened bacteria expressing Fab' antibody was selected, seeded on the 2YT-AG medium and cultured by shaking at 30° C. overnight according to the protocol of Expression Module/Recombinant Pharge Antibody System (manufactured by Amersham Pharmacia Biotech Inc.). The shaken cultured culture was added to 10-fold amount of the 2YT-AG medium and cultured by shaking at 30° C. until A600 became 0.5. The bacteria were collected by centrifugation at a room temperature and the supernatant was removed. The bacteria were suspended in the same amount of 2YT-AI (no glucose, 100 μg/ml ampicillin, 1 mM IPTG), and cultured at 30° C. overnight to induce an antibody. Then, the bacteria were precipitated by centrifugation, and the supernatant was taken. 100 μl of the culture supernatant containing anti-human alpha-1-anititrypsin Fab' antibody induced by IPTG was added to a microtiterplate for adsorbing an antigen on which the human alpha-1-anititrypsin (manufactured by Carbiochem-Novabiochem) was fixed. Then, ELISA was performed according to the protocol of HRP/Anti-E tag Conjugate (manufactured by Amersham Pharmacia Biotech Inc.) to screen bacteria expressing anti-human alpha-1-anititrypsin Fab' antibody.

(4) Transformation for Base Sequence Determination and Sequencing of an Antibody Gene A plasmid DNA was extracted from bacteria expressing anti-human alpha-1-anititrypsin Fab' antibody obtained from screening and it was transformed into the commercially available *Escherichia coli* XL10-GOLD (manufactured by Stratagene) for sequencing. XL10-GOLD transformed with the gene expressing anti-human alpha-1-anititrypsin Fab' antibody was mixed with a DNA (about 10 ng) of a vector expressing the antibody gene and stored in ice for 30 minutes according to Epicurian Coli XL10-Gold ultracompetent Cells (manufactured by Stratagene). Then, after heat-treatment at 42° C. for 30 seconds, 900 μL of NZY medium (NZ amine 10 g, yeast extract 5 g, sodium chloride 5 g, magnesium chloride 12.5 mM, magnesium sulfate 12.5 mM, glucose 20 mM:, pH 7.5: per 1 liter) was added and cultured by shaking at 37° C. for about 1 hour. The culture was spread on LB agar medium containing 50 μg/ml ampicillin (tryptone 10 g, yeast extract 5 g, sodium chloride 5 g, agar 15 g [pH 7]: per 1 liter) to select the transformed resistant strain containing gene expressing anti-human alpha-1-anititrypsin Fab' antibody.

The pCANTAB5E plasmid containing gene expressing anti-human alpha-1-anititrypsin Fab' antibody was extracted from the selected resistant strain and the base sequence of each part of the gene expressing anti-human alpha-1-anititrypsin Fab' antibody was determined by a chain terminator method using dideoxynucleotides (manufactured by Perkin Elmer) to find that an expressible open reading frame (ORF) was taken. In addition, it was confirmed that the isolated gene expressing anti-human alpha-1-anititrypsin Fab' antibody contained the Fd chain gene (gene of the VH region and the CH1 region) and the L chain gene (gene of the VL region and the CL region).

(5) Induction and Purification of an Anti-Human Alpha-1-Anititrypsin Fab' Antibody Produced by *Escherichia coli*

In order to use an anti-human alpha-1-anititrypsin Fab' antibody produced by *Escherichia coli* in an experiment described below, antibody was induced in a large scale using the screened cell strain and the resultant product was purified. That is, induction and purification of an anti-human alpha-1-anititrypsin Fab' antibody were performed according to the protocol of RPAS Purification Module (manufactured by Amersham Pharmacia Biotech Inc.).

A single colony was picked up from the screened *Escherichia coli* HB2151 strain containing the gene expressing an anti-human alpha-1-anititrypsin Fab' antibody, seeded on 2YT-AG medium, then, cultured at 30° C. overnight according to the protocol Expression Module/Recombinant Pharge Antibody System (manufactured by Amersham Pharmacia Biotech Inc.). The shaken cultured culture was added to 10-fold amount of 2YT-AG medium and cultured by shaking at 30° C. until A600 became 0.5. The bacteria were collected by centrifugation and the supernatant was removed. The bacteria were suspended in the same amount of 2YT-AI (containing no glucose) and cultured at 30° C. overnight. The bacteria were precipitated by centrifugation, the supernatant was taken, filtered with 0.45 μm filter (manufactured by Millipore), and pH was adjusted to 7 to obtain a culture supernatant.

The culture supernatant containing anti-human alpha-1-anititrypsin Fab' antibody induced by IPTG was bound to anti E-tag affinity column at a flow rate of 5 ml/minutes. 25 ml of Binding buffer attached (rate of 5 ml/min.) was flown to wash out the culture supernatant containing no antibody and anti-human alpha-1-anititrypsin Fab' antibody produced by *Escherichia coli* was eluted (rate of 5 ml/min.) with 10 ml of Elution buffer. The eluted anti-human alpha-1-anititrypsin Fab' antibody was neutralized by immediately adding 1/10 amount (relative to Elution buffer) of Neutralizing buffer. Purification was conducted by affinity chromatography using anti E-tag antibody as a ligand. The neutralized anti-human alpha-1-anititrypsin Fab' antibody was concentrated using Microcon (for fraction: molecular weight 30000) (manufactured by Millipore), dissolved in 1 ml of PSB buffer, and stored at −80° C.

(6) Fluorescently Labeling of Anti-Human Alpha-1-Anititrypsin Fab' Antibody Produced by *Escherichia coli*

Preparation of tetramethylrhodamine-5-iodoacetamide which is a fluorescent dye (fluorescent labeling agent) was performed as follows: That is, 1 mg of tetramethylrhodamine-5-iodoacetamide (manufactured by Molecular Probes) was dissolved in 0.6 ml of 50% acetonitrile, and the solution was centrifuged at 10,000 rpm for 5 minutes to remove the precipitates. The supernatant was subjected to a reverse chromatography column equilibrated with 25% acetonitrile-0.1% trifluoroacetic acid (Toso-ODS-80Ts, diameter 4.6 mm, length 25 cm), and eluted with a linear gradient of 25 to 55% acetonitrile over 30 minutes to detect by monitoring the absorbance at 280 nm. The greatest peak was taken, and the concentration thereof was determined by absorbance measurement using molecular extinction coefficient at 543 nm of 87,000. This was used for fluorescently labeling the purified anti-human alpha-1-anititrypsin Fab' antibody as purified tetramethylrhodamine-5-iodoacetamide.

The purified anti-human alpha-1-anititrypsin Fab' antibody was fluorescently labeled as follows: That is, a concentrated solution of anti-human alpha-1-anititrypsin Fab' antibody (100 μl) was diluted with 10-fold amount of a 0.1M phosphate buffer containing 5 mM EDTA (pH 7.0) and centrifuged with Microcon (for fraction molecular weight 30000) (manufactured by Millipore) to exchange the buffer. This procedure was repeated two times. 20 μl of 100 mM mercaptoethylamine (manufactured by Nakaraitesk) was added to 200 μl of anti-human alpha-1-anititrypsin Fab' antibody, the resultant mixture was stirred, and was incubated at 37° C. for 30 minutes. The mixture was concentrated again to 20 μl with Microcon (for fraction molecular weight 30000) (manufactured by Millipore) and ultrafiltered with 200' 1 of a 0.1M phosphate buffer with 5 mM EDTA (pH 7.5).

25 nmol of tetramethylrhodamine-5-iodoacetamide (manufactured by Molecular Probes) was dissolved in 5 μl of N,N-dimethylformamide (manufactured by Sigma), 75 μl of a 0.1M phosphate buffer 5 mM (with EDTA (pH 7.5)), 5 μl of 1 mM mercaptoethylamine (manufactured by Nakaraitesk) and incubated at 37° C. for 10 minutes. This was mixed with mercaptoehylamine-treated anti-human alpha-1-anititrypsin Fab' antibody to react in the dark place overnight. The reaction product was subjected to Sephadex G-25 (manufactured by Amersham Pharmacia Biotech Inc.) to separate an unreacted fluorescent dye and fluorescently labeled anti-human alpha-1-anititrypsin Fab' antibody (referred to as one molecule fluorescently labeled anti-human alpha-1-anititrypsin Fab' antibody in some cases because the antibody is labeled with one molecule of a fluorescent dye) which were used in the following experiment. The concentration of one molecule fluorescently labeled anti-human alpha-1-anititrypsin Fab' antibody was determined by absorbance measurement using molecular extinction coefficient at 543 nm of 87,000.

(7) Assessment by Isoelectric Focusing with Fluorescent Detection

The resultant one molecule fluorescently labeled anti-human alpha-1-anititrypsin Fab' antibody was separated and detected using a capillary electrophoretic apparatus P/ACE5510 manufactured by Beckman. As a capillary, a fused silica capillary (manufactured by GL Science), having an inner diameter of 0.05 mm, an external diameter of 0.375 mm, and a full length of 27 cm, that was covered with polyacrylamide covalently-bonded to the inner wall was used. Fluorescent detection was performed by laser excitation at a position of 20 cm from the anode. After the capillary was filled with an amphoteric carrier solution of Pharmalyte 3-10 (manufactured by Pharmacia BioTec, 40-fold diluted), hydroxypropyl methylcellulose (manufactured by Sigma, hereinafter referred to as HPMC, final concentration 0.125%), and N,N,N',N'-tetramethyl ethylenediamine (TEMED, manufactured by Pharmacia BioTec, final concentration 0.6%), an amphoteric carrier solution containing $2\times10^{-8}$ M one molecule fluorescently labeled anti-human alpha-1-anititrypsin Fab' antibody was injected for 30 seconds through the anode at the high pressure mode.

Figure 3:
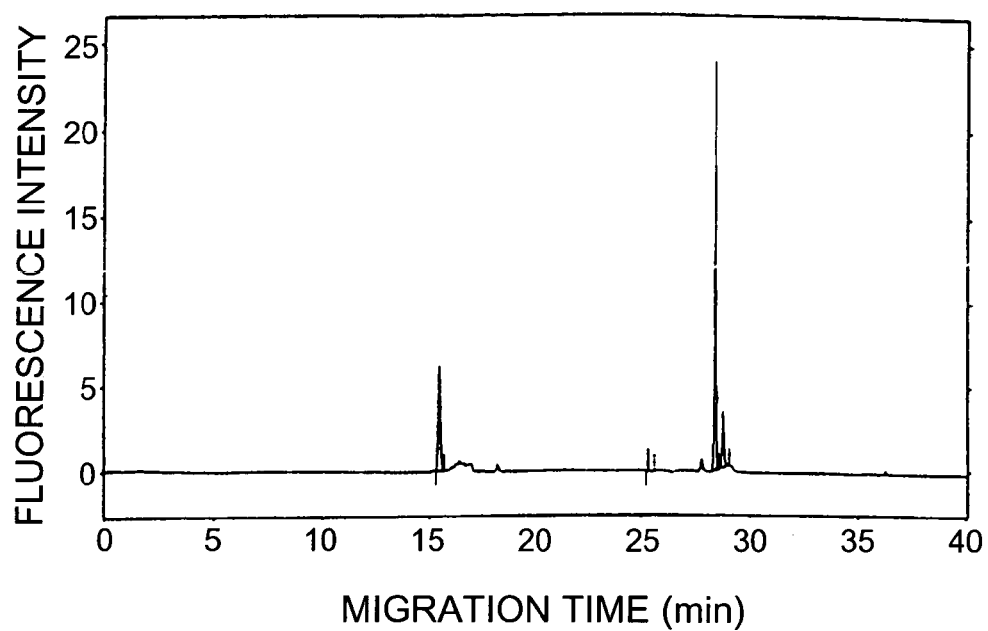
FIG. 3 is a view showing migration time and fluorescent intensity when fluorescently detecting capillary isoelectric focusing is performed using the anti-human alpha-1-antitrypsin Fab' antibody which is not modified.

After voltage of 13.5 KV (500 V/cm) was applied for 10 minutes using a 20 mM phosphoric acid containing HPMC (final concentration 0.1%) as an anode solution and 20 mM NaOH as a cathode solution, the anode solution was injected in the anode side at the low pressure mode while maintaining the same voltage, to detect one molecule fluorescently labeled anti-human alpha-1-anititrypsin Fab' antibody which was focused in the pH gradient carrier. The excitation of the fluorescent dye was performed using an argon laser (manufactured by Beckman, Laser Module 488) having a wavelength of 488 nm by mounting a 488 nm notch filter (manufactured by Beckman) and a band filter for rhodamine (manufactured by Asahibunko, especially ordered one) on the filter housing unit. The obtained results are shown in FIG. 3. As seen from FIG. 3, an isoelectric point of one molecule fluorescently labeled anti-human alpha-1-anititrypsin Fab' antibody produced by *Escherichia coli* was ununiform.

(8) Correction of an Isoelectric Point by a Site-Specific Mutagenesis

In order to correct an ununiformity of the isoelectric point of the anti-human alpha-1-antitrypsin Fab' antibody, the following DNA primers which site-specifically mutates the CH1 region were designed, and a modification of the antibody was performed. In the following experiment, for example, when converting (or having converted) N (asparagine) at the 162nd position in the H chain according to the Kabat numbering system into D (aspartic acid), the description "H-N162D" is used in some cases. Therefore, the Fab' antibody in which N (asparagine) at 162nd position in the H chain according to the Kabat numbering system was converted into D (aspartic acid) is expressed as "H-N162D modified Fab' antibody" and a gene expressing this antibody is expressed as "a gene expressing H-N162D modified Fab' antibody."

As a DNA primer, the F5-1 primer (SEQ ID NO: 5 in the Sequence Listing) and the H-N162D-BamHI primer (SEQ ID NO: 6 in the Sequence Listing) were used. In the following sequences, 5, and 3' mean a 5' side and a 3, side of the primer, respectively, S indicates C or G, M indicates A or C, R indicates A or G, and W indicates A or T.

```
F5-1 primer (SEQ ID NO: 5):
5' SAGGTSMARCTGCAGSAGTCWGG 3'

H-N162D-BamHI primer (SEQ ID NO: 6)
5' GCTGGACAGGGATCCAGAGTCCCAGGTCACTGT 3'
```

A gene fragment in which N (asparagine) at the 162nd position in the H chain according to the Kabat numbering system was converted into D (aspartic acid) was prepared by performing PCR using these primers and using the gene expressing anti-human alpha-1-anititrypsin Fab' antibody obtained in (2) as a template and the resultant product was digested with BamHI. To this digestion product was ligated to a gene fragment obtained from a low melting point agarose electrophoresis of a BamHI-digested product of the gene expressing an anti-human alpha-1-anititrypsin Fab' antibody.

In order to ligate to the same pCANTAB5E plasmid vector as that used in (2), the ligation product was subjected to PCR using the F5-2 primer and the K3-2 primer having the following sequences, then digested using SfiI and NotI restriction enzymes, and ligated to the pCANTAB5E plasmid vector to make an expression vector containing the gene expressing H-N162D modified Fab' antibody.

```
F5-2 primer (SEQ ID NO: 7):
5' CATGTGAACTGACTGGGCCCAGCCGGCCATGGCCGAGGTCCAGCTG
CAGCAGTCAGG 3'

K3-2 primer (SEQ ID NO: 8)
5' CCACGATTCTGCGGCCGCACACTCATTCCTGTTGAAGCTCTTTGTA
AT 3'
```

The aforementioned expression vector was transformed into *Escherichia coli* HB2151. An antibody was induced as described above, and screening by ELISA was performed. A plasmid was extracted from the bacteria showing a positive reaction and transformed into *Escherichia coli* XL10. The plasmid was extracted from the transformed XL10 bacteria to the amount for use in a sequencing reaction and the base sequence of gene expressing H-N162D modified Fab' antibody was confirmed. In preparation of the modified gene, the Pyrobest polymerase having the high fidelity (manufactured by Takara Shuzo) was used as a polymerase. After confirmation of the base sequence, the culturing scale of *Escherichia coli* transformed with the expression vector was extended to produce H-N162D modified Fab' antibody. The antibody obtained was purified by an affinity column to obtain a purified H-N162D modified Fab' antibody.

The sequence of the CH1 region and a part adjacent to the C-terminal of the CH1 region of H-N162D modified Fab' antibody which was confirmed by the aforementioned method is shown below (SEQ ID NO: 9 in the Sequence Listing):

AKTTPPSVYPLAPGSAAQTNSMVTLGCLVKGYFPEPVTVTW<u>D</u>SGSLSSG

VHTFPAVLQSDLYTLSSSVTVPSSTWPSETVTCNVAHPASSTKVDKKIVPR

DCGCSR

In this sequence, the sequence of C-terminal side (right side), VPRDCGCSR, is the amino acid sequence comprising a cysteine residue (C) which is not involved in binding with the L chain, and which was introduced into a part adjacent to the C-terminal of the CH1 region. Here, the cysteine residue which is not involved in binding with an L chain is the one which exists in the C-terminal side of the sequence of VPRDCGCSR. In addition, a part other than the sequence of VPRDCGCSR is the sequence of the CH1 region.

The sequence of the corresponding part in the Fab' antibody before H-N162D modification is performed is as follows (SEQ ID NO: 10):

AKTTPPSVYPLAPGSAAQTNSMVTLGCLVKGYFPEPVTVTW<u>N</u>SGSLSSG

VHTFPAVLQSDLYTLSSSVTVPSSTWPSETVTCNVAHPASSTKVDKKIVPR

DCGCSR

When the above two sequences are compared, it is found that the asparagine residue (underlined N) at the 162nd position in the H chain according to the Kabat numbering system is converted into aspartic acid (underlined D) after modification. In addition, in this Example, the sequence of a part adjacent to the C-terminal of the CH1 region in H-N162D modified Fab' antibody (VPRDCGCSR) is the same as the sequence of a part adjacent to the C-terminal of the CH1 region in an Fab' antibody before H-N162D modification (VPRDCGCSR).

(9) Separation and Detection of a Fluorescently Labeled Fab' Antibody Having a Uniform Isoelectric Point by Fluorescent Detection Capillary Isoelectric Focusing The H-N162D modified Fab' antibody obtained in (8) was fluorescently labeled with tetramethylrhodamine-5-iodoacetamide (manufactured by Molecular Probes) according to the same manner as that described in (6), to obtain one molecule fluorescently labeled Fab' antibody. This one molecule fluorescently labeled Fab' antibody was separated and detected using the capillary electrophoretic apparatus P/ACE5510 manufactured by Beckman according to the same manner as that of (7). The results thereof are shown in FIG. 4.

Figure 4:
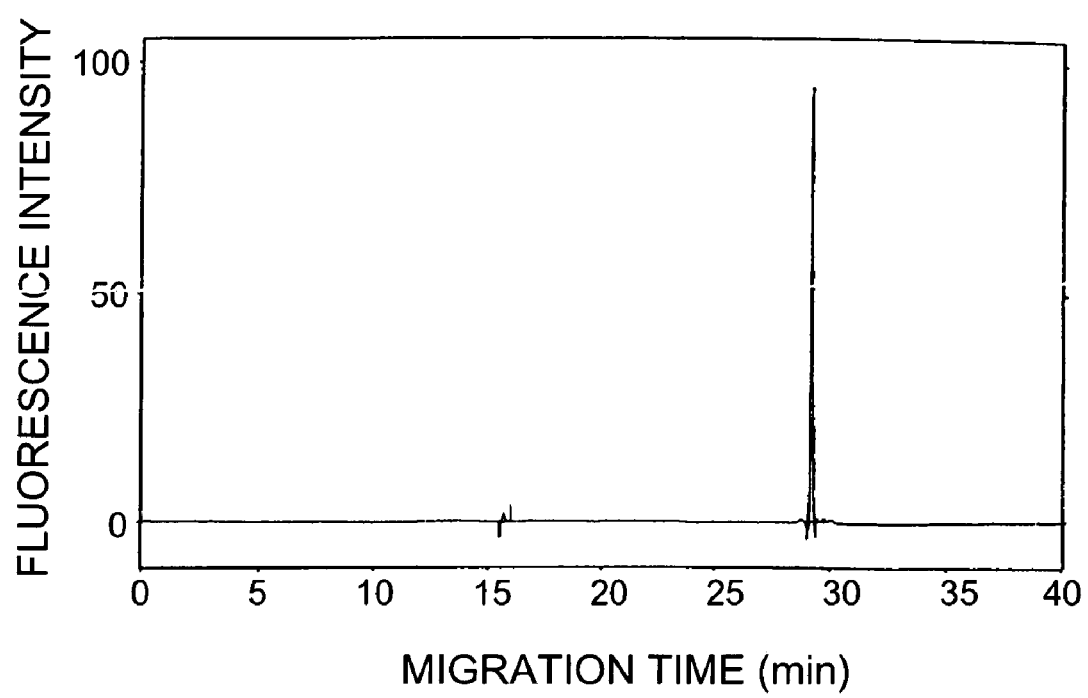
FIG. 4 is a view showing migration time and fluorescent intensity when fluorescently detecting capillary isoelectric focusing is performed using the modified anti-human alpha-1-antitrypsin Fab' antibody (H-N162D modified Fab' antibody).

As seen from FIG. 4, in the case where one molecule fluorescently labeled H-N162D modified Fab' antibody is subjected to capillary electrophoresis, one large peak appeared near an migration time of 29 minutes and no substantial peak appeared at other areas. This means that the isoelectric point of H-N162D modified Fab' antibody is uniform.

(10) Modification by Adding an Amino Acid Sequence Comprising a Charged Amino Acid Residue In order to add an amino acid sequence comprising a charged amino acid residue adjacent to the C-terminal of the L chain of the H-N162D modified Fab' antibody obtained in (8), a DNA primer for introducing an amino acid sequence comprising a charged amino acid residue was designed. A gene expressing the H-N162D modified Fab' antibody which is modified by adding an amino acid sequence comprising a charged amino acid residue adjacent to the C-terminal of the L chain (Hereinafter, this gene may be called a gene expressing a charge modified H-N162D modified Fab' antibody.) was obtained by performing PCR using the gene expressing the H-N162D modified Fab' antibody as a template and using the above-described DNA primers. As a DNA primer, F5-1 primer (SEQ ID NO: 5) described above, F5-2 primer (SEQ ID NO: 7) described above, and K3+5RPS primer (SEQ ID NO: 11) shown below were used.

```
K3+5RPS primer (SEQ ID NO: 11):
5' GGTGATCGGCCCCCGAGGCCGGTCTACTTGGTCGACTTGGTCGACTAG
GTCTAGAAGGACGTGAACACTCATTCCTGTTGAAGCTC 3'
```

After the gene expressing a charge modified H-N162D modified Fab' antibody is digested with a restriction enzyme of SfiI, or SfiI/NotI, the resultant gene was ligated to a plasmid vector for expressing a protein (pCANTAB5E plasmid vector or the like). Then, an expression vector containing the gene expressing a charge modified H-N162D modified Fab' antibody was produced.

The aforementioned expression vector was transformed into Escherichia coli HB2151. An antibody was induced as described above, and screening by ELISA was performed. A plasmid was extracted from the bacteria showing a positive reaction and transformed into Escherichia coli XL10. The plasmid was extracted from the transformed XL10 bacteria to the amount for use in a sequencing reaction and the base sequence of the gene expressing a charge modified H-N162D modified Fab' antibody was confirmed. In preparation of the modified gene, the Pyrobest polymerase having the high fidelity (manufactured by Takara Shuzo) was used as a polymerase. After confirmation of the base sequence, the culturing scale of Escherichia coli transformed with the expression vector was extended to produce H-N162D modified Fab' antibody which is modified by adding an amino acid sequence comprising a charged amino acid residue (Hereinafter, this may be called a charge modified H-N162D modified Fab' andibody). Then, this antibody was purified by an affinity column to obtain the purified antibody.

The sequence (SEQ ID NO: 12 in the Sequence Listing) of the CL region and a part adjacent to the C-terminal of the CL region (the C-terminal of the L chain) of the charge modified H-N162D modified Fab' andibody which was confirmed by the aforementioned method is shown below:

```
ADAAPTVSIFPPSSEQLTSGGASVVCFLNNFYPKDINVKWKIDGSERQN
GVLNSWTDQDSKDSTYSMSSTLTLTKDEYERHNSYTCEATHKTSTSPITKS
FNRNECSRPSRPSRPSRPSRP
```

In this sequence, the sequence of the C-terminal side (right side) SRPSRPSRPSRPSRP is the amino acid sequence comprising a charged amino acid residue which is added adjacent to the C-terminal of the CL region (the C-terminal of the L chain). In this sequence, the sequence of SRP is repeated 5 times, and R (arginine) is the charged amino acid residue. In addition, a part other than the sequence of SRPSRPSRPSRPSRP is as follows:

```
ADAAPTVSIFPPSSEQLTSGGASVVCFLNNFYPKDINVKWKIDGSERQN
GVLNSWTDQDSKDSTYSMSSTLTLTKDEYERHNSYTCEATHKTSTSPITKS
FNRNEC
```

This sequence is the sequence (SEQ ID NO: 13) of the CL region.

(11) Separation and Detection by Fluorescently Detecting Capillary Isoelectric Focusing of Immune Complex The H-N162D modified Fab' antibody obtained in (8) was fluorescently labeled with tetramethylrhodamine-5-iodoacetamide (manufactured by Molecular Probes) according to the same manner as that described in (6). The resultant antibody may be called one molecule fluorescently labeled Fab' antibody having a uniform isoelectric point hereinafter. The charge modified H-N162D modified Fab' antibody obtained in (10) was also fluorescently labeled with tetramethylrhodamine-5-iodoacetamide (manufactured by Molecular Probes) according to the same manner as that described in (6). The resultant antibody may be called one molecule fluorescently labeled charge modified Fab' antibody having a uniform isoelectric point.

The concentration of the fluorescently labeled Fab' antibody having a uniform isoelectric point and the fluorescently labeled charge modified Fab' antibody having a uniform isoelectric point was determined by absorbance measurement using molecular extinction coefficient at 543 nm of 87,000. These antibodies were (1) concentrated by centrifugation using microcon-10 (fractionation molecular weight 10,000) (Millipore Co.), (2) charged with high pressure steam-sterilized MilliQ water, and (3) centrifuged. Above steps (1)–(3) were repeated twice for deionization. The resultant product was charged with high pressure steam-sterilized MilliQ water to reach the final concentration of 80 nM.

The human alpha-1-antitrypsin (Carbiochem Co.) dissolved in high pressure steam-sterilized MilliQ water was (1) concentrated by centrifugation using microcon-10 (fractionation molecular weight 10,000) (Millipore Co.), (2)

charged with high pressure steam-sterilized MilliQ water, and (3) centrifuged. Above steps (1)–(3) were repeated twice for deionization. The resultant product was charged with high pressure steam-sterilized MilliQ water to reach the final concentration of 8 µM.

The same amount of the solution of fluorescently labeled Fab' antibody having a uniform isoelectric point and the solution of the human alpha-1-antitrypsin were mixed. The mixed solution was mixed with the same amount of Phrmalyte 3-10 (Amersham pharmacia biotech Co., 20-fold diluted solution) and hydroxypropyl methylcellulose (Sigma Co., final concentration: 0.8%). The mixture was kept dark at room temperature for 10 minutes to obtain an immune complex. The same procedure was applied to the fluorescently labeled charge modified Fab' antibody having a uniform isoelectric point to obtain an immune complex. The resultant solution was separated and detected using a capillary electrophoretic apparatus P/ACE5510 manufactured by Beckman.

Figure 5:
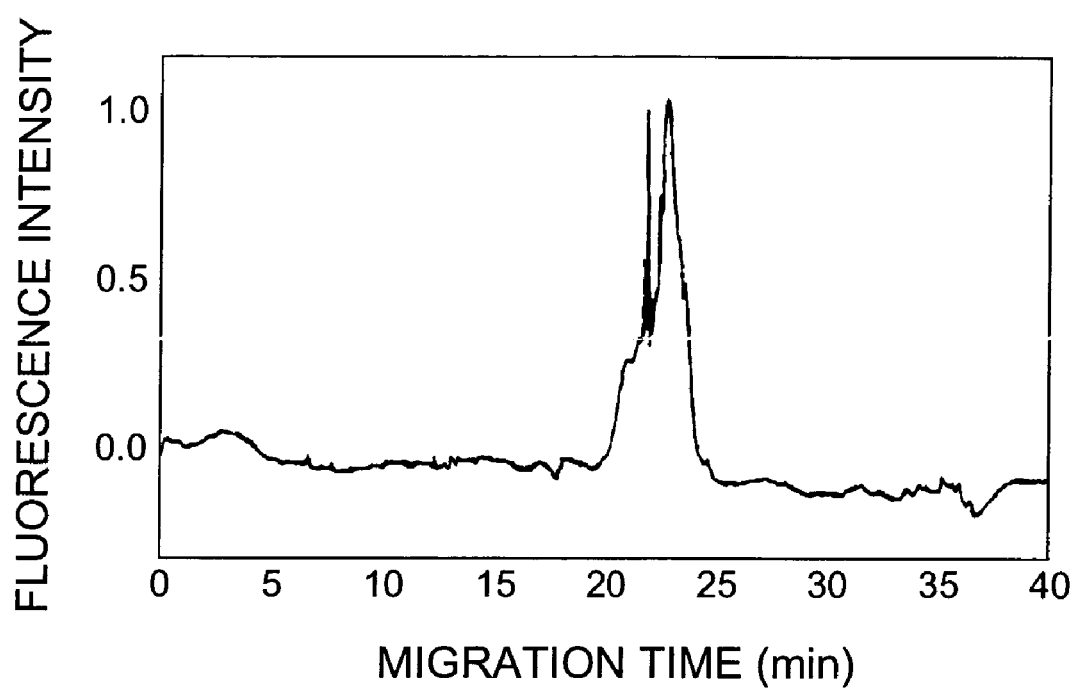
FIG. 5 is a view showing migration time and fluorescence intensity when electrophoresis is performed to the immune complex comprising the Fab' antibody having a uniform isoelectric point and the antigen.
Figure 6:
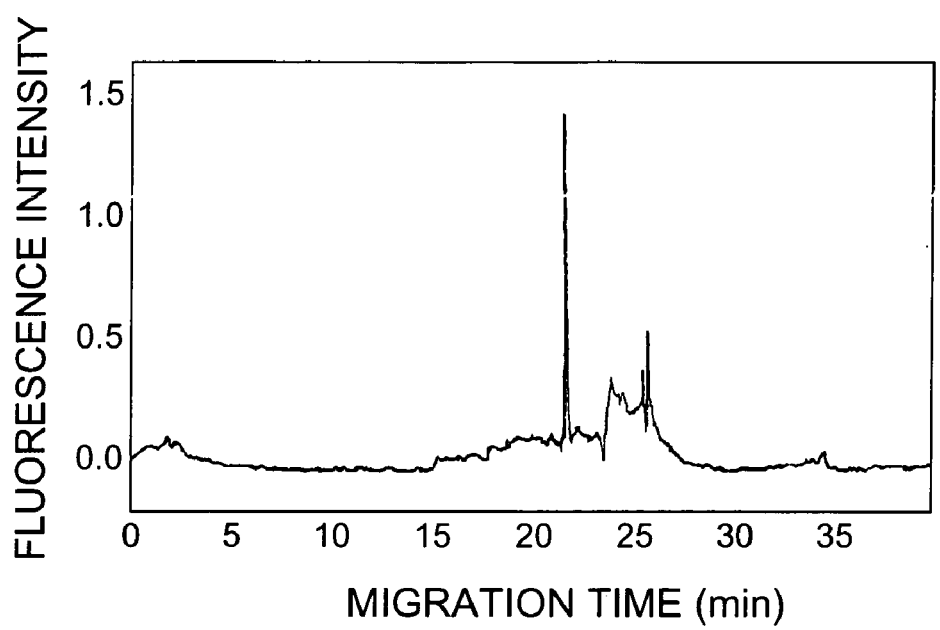
FIG. 6 is a view showing migration time and fluorescence intensity when electrophoresis is performed to the immune complex comprising the Fab' antibody having a uniform isoelectric point which is modified by adding an amino acid sequence comprising a charged amino acid residue, and the antigen.

The result of the example using the fluorescently labeled Fab' antibody having a uniform isoelectric point was shown in FIG. 5, while the result of the example using the fluorescently labeled charge modified Fab' antibody having a uniform isoelectric point is shown in FIG. 6. In FIG. 5, a large peak appeared at a migration time of about 22 minutes overlaps peaks appeared at a migration time of 20–25 minutes. Therefore, separation is insufficient. On the other hand, in FIG. 6, a large peak appeared at a migration time of about 22 minute is clearly separated from peaks appeared at a migration time of 24 minutes and greater.

A schematic view of the method for quantitatively detecting an antigen according to the present invention is shown in FIGS. 7A–D, which include steps for producing the Fab' antibody having a uniform isoelectric point. FIG. 7A shows *Escherichia coli* in which the gene expressing an Fab' antibody having a uniform isoelectric point of the present invention is incorporated and an antibody is induced by acting IPTG (isopropyl-β-D-thiogalactopyranoside) on this *Escherichia coli*. FIG. 7B shows the Fab' antibody having a uniform isoelectric point of the present invention produced by this antibody induction. This Fab' antibody having a uniform isoelectric point is purified with an affinity column or the like and, thereafter, fluorescently labeled. FIG. 7C shows this fluorescently labeled Fab' antibody having a uniform isoelectric point. Upon performing electrophoresis of the immune complex formed by the fluorescently labeled Fab' antibody having a uniform isoelectric and an antigen, the data about the relation between migration time and fluorescence intensity, as shown in FIG. 7D, is obtained.

A schematic view of the method for quantitatively detecting an antigen according to the conventional method disclosed in JP-A 8-506182 is shown FIGS. 8A–G, which include steps for producing the Fab' antibody having a uniform isoelectric point. By comparing FIGS. 7A–D and FIGS. 8A–G, it is apparent that the conventional method includes a lot of steps, which are cumbersome, to obtain the Fab' antibody having a uniform isoelectric point. Further, in the conventional method, when the isoelectric point of an antigen is close to that of the fluorescently labeled Fab' antibody having a uniform isoelectric point, migration time of the immune complex becomes almost the same as those of the excessive antigen and/or antibody. Therefore, peaks are overlapped and detection can not be performed with high accuracy.

On the other hand, the method for quantitatively detecting an antigen according to the present invention, as shown in FIGS. 7A–D, includes simple steps to obtain the Fab' anibody having a uniform isoelectric point. And the method according to the present invention enables a detection with high accuracy even when the isoelectric point of the antigen is close to that of the Fab' antibody having a uniform isoelectric point.

INDUSTRIAL APPLICABILITY

As explained above, according to the present invention, there can be provided a method for quantitatively detecting an antigen which enables a detection with high accuracy even when an isoelectric point of an antigen as an analyte is close to an isoelectric point of a fluorescently labeled antibody.

The invention claimed is:

1. A method for quantitatively detecting an antigen in an analytical sample, said analytical sample suspected of containing an amount of antigen, which comprises:

a) providing a plurality of identical modified recombinant Fab' antibodies having a uniform isoelectric point, each said modified antibody being specific for the antigen and capable of forming an immune complex with any of the antigen in the analytical sample, and each said modified Fab' antibody being recombinantly modified from a first antigen specific antibody in having:

i) at least one additional charged amino acid residue adjoined to a L-chain C-terminus;

ii) a site specific mutation in encoding nucleic acid altering at least one Fd-chain CH1 region amide side chain-containing amino acid residue in said first antibody to a non-amide side chain-containing amino acid residue, except cysteine, in said modified antibody;

iii) a single cysteine residue, which is not involved in binding of the Fd-chain to the L-chain, in an amino acid sequence adjoining the Fd-chain CH1 region C-terminus in the modified Fab' antibody; and iv) a fluorescent dye label bound to the single non-L-chain binding cysteine residue;

b) contacting the plurality of modified Fab' antibodies having a uniform isoelectric point with the analytical sample in a mixture under conditions sufficient for formation of said immune complexes;

c) separating any formed immune complexes from unbound antibodies and antigen by performing electrophoresis of the mixture in a carrier;

d) irradiating the electrophoresed mixture in the carrier with an excitation light which excites the fluorescent dye label;

e) detecting a level of fluorescence of the separated and irradiated immune complexes or the separated and irradiated unbound antibodies; and f) correlating the detected level of fluorescence with the amount of antigen in the analytical sample.

2. The method of claim 1 wherein correlating the detected level of fluorescence involves comparing the detected level of fluorescence with a standard curve relating fluorescence intensity with amount of antigen.

3. The method of claim 1 wherein the electrophoresis is performed by isoelectric focusing.

4. The method of claim 1 wherein the electrophoresis is performed by capillary electrophoresis.

* * * * *

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
saggtsmarc tgcagsagtc wgg                                          23

<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
gcgtcatcta gaacaaccac aatccctggg caca                              34
```

<210> SEQ ID NO 3
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: "n" can be a, t, g, or c
<220> FEATURE:
<221> NAME/KEY: misc_feature
<222> LOCATION: (23)..(23)
<223> OTHER INFORMATION: "n" can be a, t, g, or c
<220> FEATURE:
<221> NAME/KEY: misc_feature
<222> LOCATION: (27)..(27)
<223> OTHER INFORMATION: "n" can be a, t, g, or c

<400> SEQUENCE: 3
ccagwtsyga gctcswbnts acncagnmdy ch                                     32

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
acactcattc ctgttgaagc t                                                 21

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
saggtsmarc tgcagsagtc wgg                                               23

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
gctggacagg gatccagagt cccaggtcac tgt                                    33

<210> SEQ ID NO 7
<211> LENGTH: 57
<212> TYPE: DNA
<213> ORGANISM: Artificial Sequence
<220> FEATURE:
<223> OTHER INFORMATION: Primer

<400> SEQUENCE: 7
catgtgaact gactgggccc agccggccat ggccgaggtc cagctgcagc agtcagg          57

<210> SEQ ID NO 8
<211> LENGTH: 48
<212> TYPE: DNA
<213> ORGANISM: Artificial Sequence
<220> FEATURE:

<223> OTHER INFORMATION: Primer

<400> SEQUENCE: 8

```
ccacgattct gcggccgcac actcattcct gttgaagctc tttgtaat              48
```

<210> SEQ ID NO 9
<211> LENGTH: 106
<212> TYPE: PRT
<213> ORGANISM: Mouse

<400> SEQUENCE: 9

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asp Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Ser Arg
            100                 105
```

<210> SEQ ID NO 10
<211> LENGTH: 106
<212> TYPE: PRT
<213> ORGANISM: Mouse

<400> SEQUENCE: 10

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Ser Arg
            100                 105
```

<210> SEQ ID NO 11
<211> LENGTH: 86
<212> TYPE: DNA
<213> ORGANISM: Artificial Sequence
<220> FEATURE:
<223> OTHER INFORMATION: Primer

<400> SEQUENCE: 11

```
ggtgatcggc ccccgaggcc ggtctacttg gtcgacttgg tcgactaggt ctagaaggac    60
gtgaacactc attcctgttg aagctc                                        86
```

-continued

```
<210> SEQ ID NO 12
<211> LENGTH: 121
<212> TYPE: PRT
<213> ORGANISM: Mouse

<400> SEQUENCE: 12

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Thr Lys Ser Phe Asn Arg Asn Glu Cys Ser Arg Pro Ser Arg Pro
            100                 105                 110

Ser Arg Pro Ser Arg Pro Ser Arg Pro
            115                 120

<210> SEQ ID NO 13
<211> LENGTH: 106
<212> TYPE: PRT
<213> ORGANISM: Mouse

<400> SEQUENCE: 13

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Thr Lys Ser Phe Asn Arg Asn Glu Cys
            100                 105
```